US009999364B2

(12) United States Patent
Chen

(10) Patent No.: US 9,999,364 B2
(45) Date of Patent: Jun. 19, 2018

(54) SYSTEMS AND METHODS FOR PROVIDING CARDIAC ELECTROPHYSIOLOGICAL MARKERS

(71) Applicant: Guangren Chen, Porter Ranch, CA (US)

(72) Inventor: Guangren Chen, Porter Ranch, CA (US)

(*) Notice: Subject to any disclaimer, the term of this patent is extended or adjusted under 35 U.S.C. 154(b) by 0 days. days.

(21) Appl. No.: 15/393,135

(22) Filed: Dec. 28, 2016

(65) Prior Publication Data

US 2017/0105642 A1 Apr. 20, 2017

Related U.S. Application Data

(63) Continuation-in-part of application No. 14/749,697, filed on Jun. 25, 2015, now Pat. No. 9,538,930, which is a continuation-in-part of application No. 14/662,996, filed on Mar. 19, 2015, now Pat. No. 9,339,204, which is a continuation of application No. PCT/US2015/020828, filed on Mar. 16, 2015.

(60) Provisional application No. 62/271,704, filed on Dec. 28, 2015, provisional application No. 62/271,699, filed on Dec. 28, 2015, provisional application No. 62/017,185, filed on Jun. 25, 2014, provisional application No. 62/008,435, filed on Jun. 5, 2014.

(51) Int. Cl.
*A61B 5/04* (2006.01)
*A61B 5/0408* (2006.01)
*A61B 5/042* (2006.01)
*A61B 5/044* (2006.01)
*A61B 5/00* (2006.01)
*A61B 5/0245* (2006.01)
*A61B 5/0452* (2006.01)

(52) U.S. Cl.
CPC ........ *A61B 5/04014* (2013.01); *A61B 5/0245* (2013.01); *A61B 5/044* (2013.01); *A61B 5/04017* (2013.01); *A61B 5/0422* (2013.01); *A61B 5/0452* (2013.01); *A61B 5/04085* (2013.01); *A61B 5/6823* (2013.01)

(58) Field of Classification Search
CPC .............. A61B 5/0245; A61B 5/04014; A61B 5/04017; A61B 5/04085; A61B 5/0422; A61B 5/044; A61B 5/0452; A61B 5/6823; A61B 5/0006; A61B 5/6869; A61B 7/04
See application file for complete search history.

(56) References Cited

U.S. PATENT DOCUMENTS

2006/0200034 A1* 9/2006 Ricci .................. G06K 9/00523
600/513

* cited by examiner

*Primary Examiner* — George Manuel
(74) *Attorney, Agent, or Firm* — John R. Kasha; Kelly L. Kasha; Kasha Law LLC

(57) ABSTRACT

Systems and methods are provided to detect a multi-domain ECG waveform and display one or more cardiac electrophysiological markers. Electrical impulses are detected between at least one pair of electrodes adapted to be located near a beating heart and are converted to an ECG waveform. The ECG waveform for at least one heartbeat is received from the detector, the ECG waveform is converted to a frequency domain waveform, the frequency domain waveform is separated into two or more different frequency domain waveforms using two or more different bandpass filters, and the two or more different frequency domain waveforms are converted into two or more different time domain waveforms. The two or more different time domain waveforms are displayed in the same time domain plot as the ECG waveform and one or more cardiac electrophysiological markers are displayed along the x-axis of the two or more different time domain waveforms.

20 Claims, 34 Drawing Sheets

SYSTEMS AND METHODS FOR PROVIDING CARDIAC ELECTROPHYSIOLOGICAL MARKERS

CROSS REFERENCE TO RELATED APPLICATION

This application is a continuation in part of U.S. patent application Ser. No. 14/749,697, filed Dec. 10, 2015, which is a continuation in part of U.S. patent application Ser. No. 14/662,996, filed Mar. 19, 2015, now U.S. Pat. No. 9,339,204, which is a continuation of PCT Application No. PCT/US15/20828, filed Mar. 16, 2015, which claims the benefit of U.S. Provisional Patent Application Ser. No. 62/008,435, filed Jun. 5, 2014; this application claims the benefit of U.S. Provisional Patent Application Ser. No. 62/271,704, filed Dec. 28, 2015, and U.S. Provisional Patent Application Ser. No. 62/271,699, filed Dec. 28, 2015; and U.S. patent application Ser. No. 14/749,697 claims the benefit of U.S. Provisional Patent Application Ser. No. 62/017,185, filed Jun. 25, 2014, the content of all of which is incorporated by reference herein in their entireties.

INTRODUCTION

Electrical signals produced by a human heart were observed through electrodes attached to a patient's skin as early as 1879. Between 1897 and 1911 various methods were used to detect these electrical signals and record a heartbeat in real-time. In 1924, Willem Einthoven was awarded the Nobel Prize in medicine for identifying the various waveforms of a heartbeat and assigning the letters P, Q, R, S, T, U, and J to these waveforms. Since the early 1900s the equipment used for electrocardiography (ECG or EKG) has changed. However, the basic waveforms detected and analyzed have not changed.

An ECG device detects electrical impulses or changes in the electrical potential between two electrodes attached to the skin of a patient as the heart muscle contracts or beats. Electrically, the contraction of the heart is caused by depolarization and repolarization of various parts of the heart muscle. Initially, or at rest, the muscle cells of the heart have a negative charge. In order to cause them to contract, they receive an influx of positive ions $Na^+$ and $Ca^{++}$. This influx of positive ions is called depolarization. The return of negative ions to bring the heart back to a resting state is called repolarization. Depolarization and repolarization of the heart affects different parts of the heart over time giving rise to the P, Q, R, S, T, U, and J waveforms.

FIG. 2 is an exemplary plot 200 of the P, Q, R, S, and T waveforms of a conventional ECG waveform of a heartbeat from a conventional ECG device. The P, Q, R, S, and T waveforms represent electrical conduction through a heart muscle. P waveform 210 represents the propagation of depolarization from the sinoatrial node, to the right and left atriums, and to the atrioventricular node. The sinoatrial node is also referred to as the sinus node, SA node, or SAN. The atrioventricular node is also referred to as the AV node or AVN. The right atrium is also referred to as the RA, and the left atrium is also referred to as the LA.

FIG. 3 is an exemplary diagram 300 of the depolarization of the muscle tissue of a heart that produces P waveform 210 of FIG. 2 as detected by a conventional ECG device. P waveform 210 of FIG. 2 is produced as depolarization propagates from SAN 310 to AVN 340 in FIG. 3. As depolarization propagates from SAN 310 to AVN 340, it also spreads from RA 320 to LA 340. P waveform 210 of FIG. 2 typically has a duration of 80 ms, for example.

PR segment 220 of FIG. 2 represents the propagation of depolarization from the AVN to the Bundle of His, and then to the Bundle Branches. PR segment 230 may also include depolarization to the Purkinje fibers of the inner ventricular walls. The Bundle of His is also referred to as the His Bundle or His. The Bundle Branches include the right bundle branches (RBB) and the left bundle branches (LBB). As shown in FIG. 2, in a conventional ECG, PR segment 220 shows up as a flat line or waveform with no amplitude.

FIG. 4 is an exemplary diagram 400 of the depolarization of the muscle tissue of a heart that produces PR segment 220 of FIG. 2 as detected by a conventional ECG device. PR segment 220 of FIG. 2 is produced as depolarization propagates from AVN 340 to His 450 and then to Bundle Branches 460 that include RBB 461 and LBB 462. PR segment 220 of FIG. 2 typically has a duration of between 50 and 120 ms, for example.

Waveforms Q 230, R 240, and S 250 of FIG. 2 form the QRS complex. The QRS complex represents the propagation of depolarization through the right and left ventricles. The right ventricle is also referred to as RV, and the left ventricle is referred to as LV.

FIG. 5 is an exemplary diagram 500 of the depolarization of the muscle tissue of a heart that produces Q waveform 230, R waveform 240, and S waveform 250 of FIG. 2 as detected by a conventional ECG device. Waveforms Q 230, R 240, and S 250 of FIG. 2 produced as depolarization propagates from Bundle Branches 460 through RV 571 and LV 572. RV 571 and LV 572 have the largest muscle mass in the heart. The QRS complex formed by waveforms Q 230, R 240, and S 250 of FIG. 2 typically has a duration of between 80 and 100 ms, for example.

ST segment 260 of FIG. 2 represents the period during which the ventricles remain depolarized and contracted. As shown in FIG. 2, in a conventional ECG, ST segment 260 shows up as a flat line or waveform with no amplitude. ST segment 260 typically has a duration of between 80 and 120 ms, for example.

The point in FIG. 2 at which the QRS complex ends and ST segment 260 begins is called J point 255. A J waveform (not shown) can sometimes appear as an elevated J point at J point 255 or as a secondary R waveform. A J waveform is usually characteristic of a specific disease. The J waveform is also referred to as the Osborn wave, camel-hump sign, late delta wave, hathook junction, hypothermic wave, prominent J wave, K wave, H wave or current of injury.

T waveform 270 of FIG. 2 represents the repolarization or recovery of the ventricles. T waveform 270 typically has a duration of 160 ms, for example. The interval between the Q and T waveforms is referred to as the QT interval.

FIG. 6 is an exemplary diagram 600 of the repolarization of the muscle tissue of a heart that produces T waveform 270 of FIG. 2 as detected by a conventional ECG device. As shown in FIG. 6, RV 571 and LV 572 are repolarized.

Not shown in FIG. 2 is the U waveform. The U waveform sometimes appears after the T waveform. The U waveform is thought to represent repolarization of the interventricular septum, the papillary muscles, or the Purkinje fibers.

As shown in FIGS. 3 through 6, as a heart beats, electrical signals flow through all the different muscle tissues of the heart. As shown in FIG. 2, for the last 100 years conventional ECG devices have been able to detect some of these signals in the form of the P, Q, R, S, T, U, and J waveforms. These waveforms have aided in the diagnosis and treatment of many heart problems. Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DETAILED DESCRIPTION

Computer-Implemented System

Figure 1:
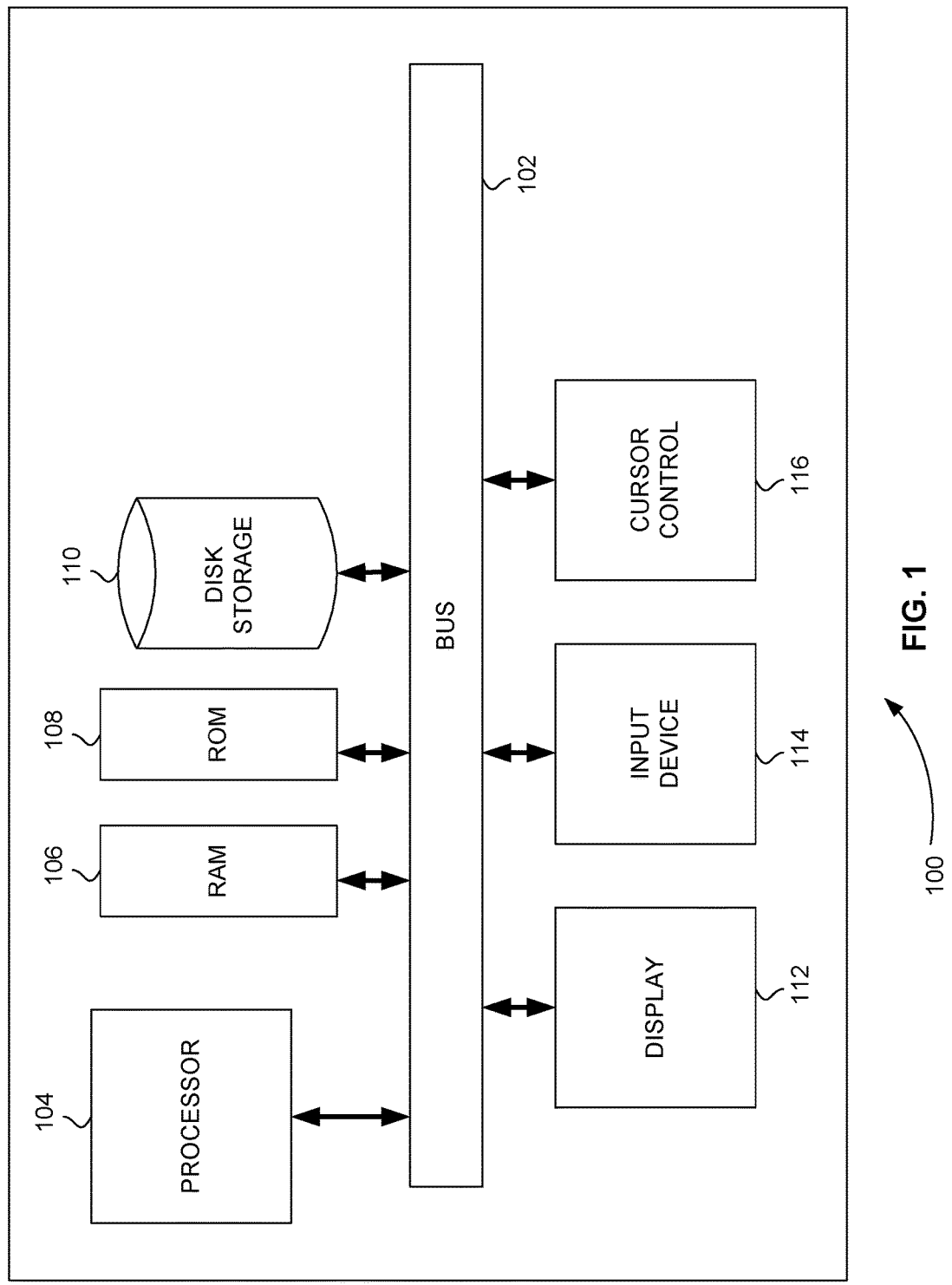
FIG. 1 is a block diagram that illustrates a computer system, in accordance with various embodiments.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Subwaveform Detection of the P, Q, R, S, T, U, and J waveforms

As described above, electrical signals flow through all the different muscle tissues of the heart. For the last 100 years, conventional ECG devices have been able to detect some of these signals in the form of the P, Q, R, S, T, U, and J waveforms. These waveforms have aided in the diagnosis and treatment of many heart problems.

Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

In various embodiments, additional information is obtained from the electrical signals produced by a heart through signal processing. More specifically, signal processing is added to an ECG device in order to detect more information from the electrical signals that flow through all the different muscle tissues of the heart as it is beating.

Figure 7:
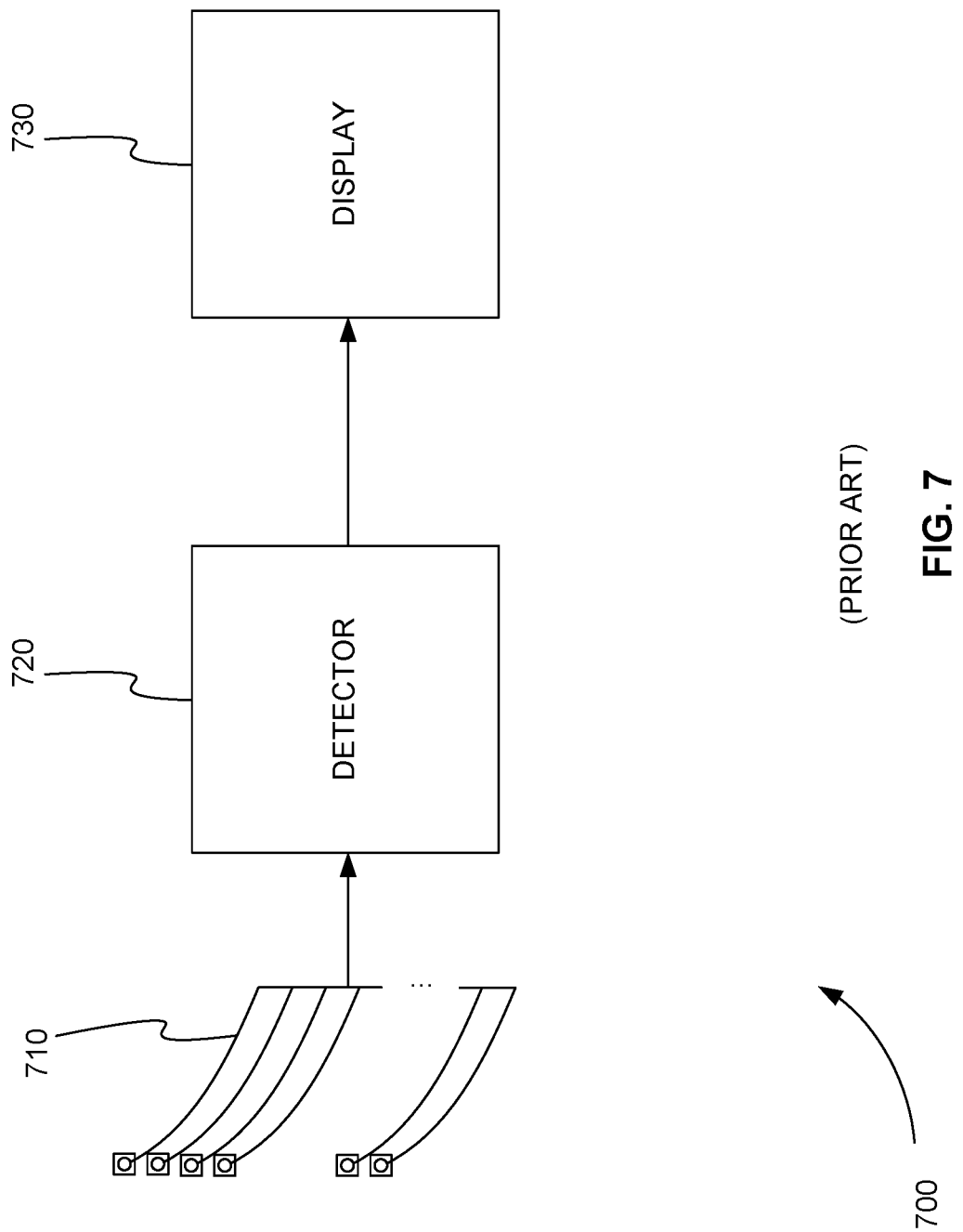
FIG. 7 is a block diagram of a conventional ECG device.

FIG. 7 is a block diagram 700 of a conventional ECG device. The conventional ECG device includes two or more leads or electrodes 710. Electrodes 710 are typically attached to the skin of a patient. Electrical signals produced by a beating heart are detected between pairs of electrodes 710. Because the heart is three-dimensional, electrodes are attached at different locations on a body to detect signals at different corresponding locations or angles from the heart. In other words, the electrodes are placed on a body to partially surround the heart. One typical type of ECG includes 12 electrodes, for example.

A voltage signal is detected between two electrodes 710 by detector 720. Detector 720 also typically amplifies the voltage signal. Detector 720 can also convert the voltage signal to a digital voltage signal using an analog to digital converter (A/D).

Detector 720 provides the detected and amplified voltage signal from each pair of electrodes 710 to display 730. Display 730 can be an electronic display device including, but not limited to, a cathode ray tube (CRT) device, light emitting diode (LED) device, or Liquid crystal display (LCD) device. Display 730 can also be a printer device. Additionally, display 730 can include a memory device to record detected signals. The memory device can be, but is not limited to, a volatile electronic memory, such as random access memory (RAM), a non-volatile electronic memory, such as electrically erasable programmable read-only memory (EEPROM or Flash memory), or a magnetic hard drive.

Figure 2:
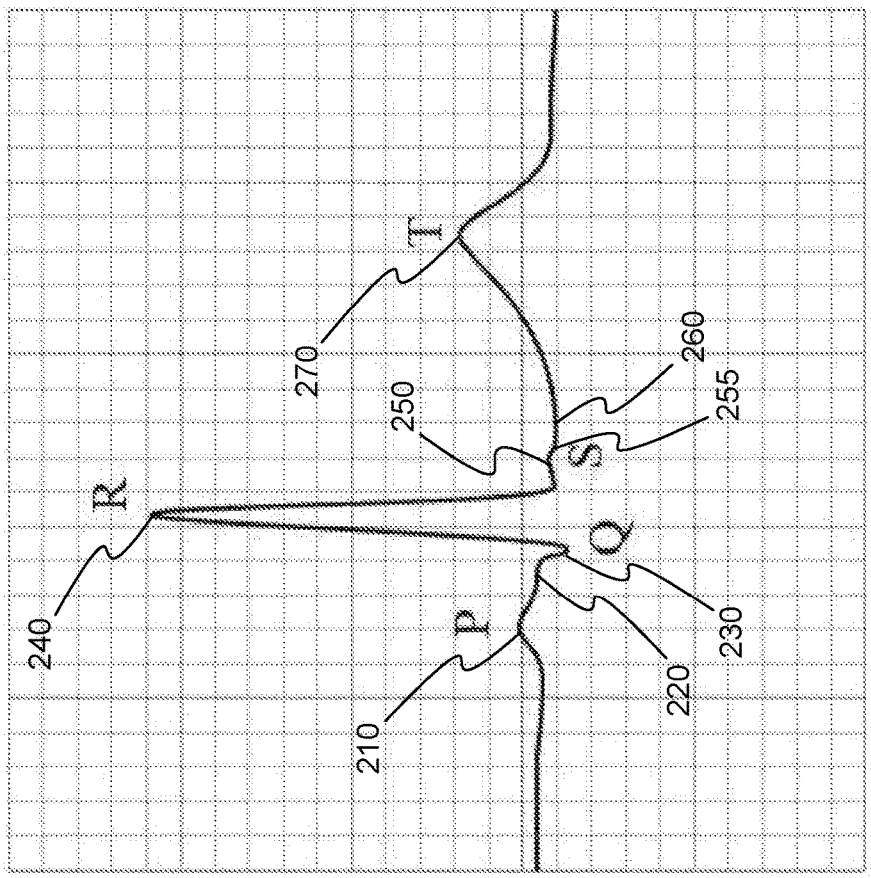
FIG. 2 is an exemplary plot of the P, Q, R, S, and T waveforms of a conventional electrocardiography (ECG) waveform of a heartbeat from a conventional ECG device.
Figure 3:
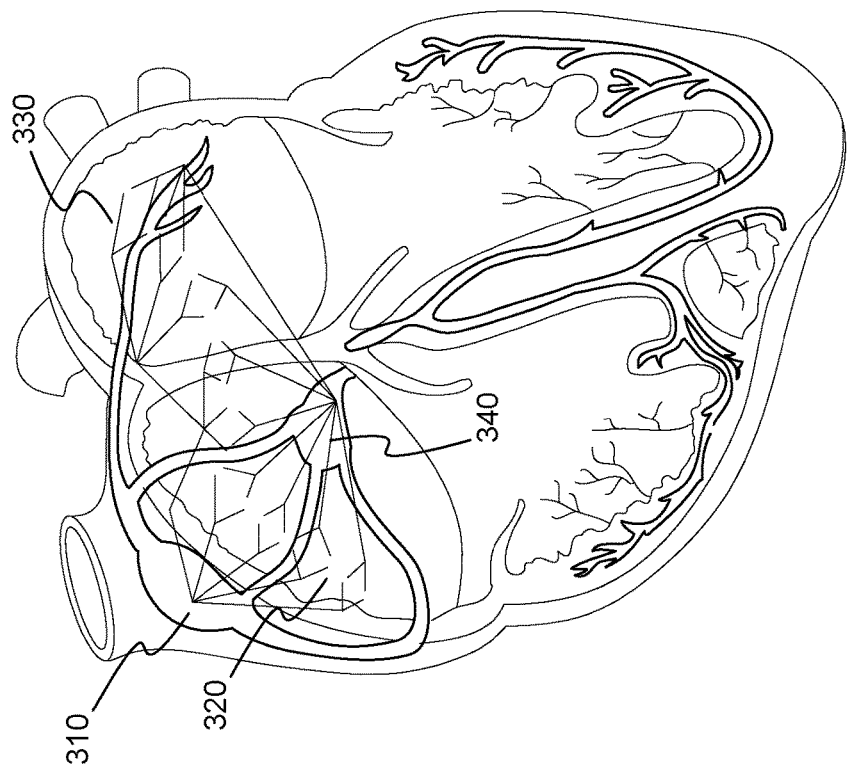
FIG. 3 is an exemplary diagram of the depolarization of the muscle tissue of a heart that produces the P waveform of FIG. 2 as detected by a conventional ECG device.
Figure 4:
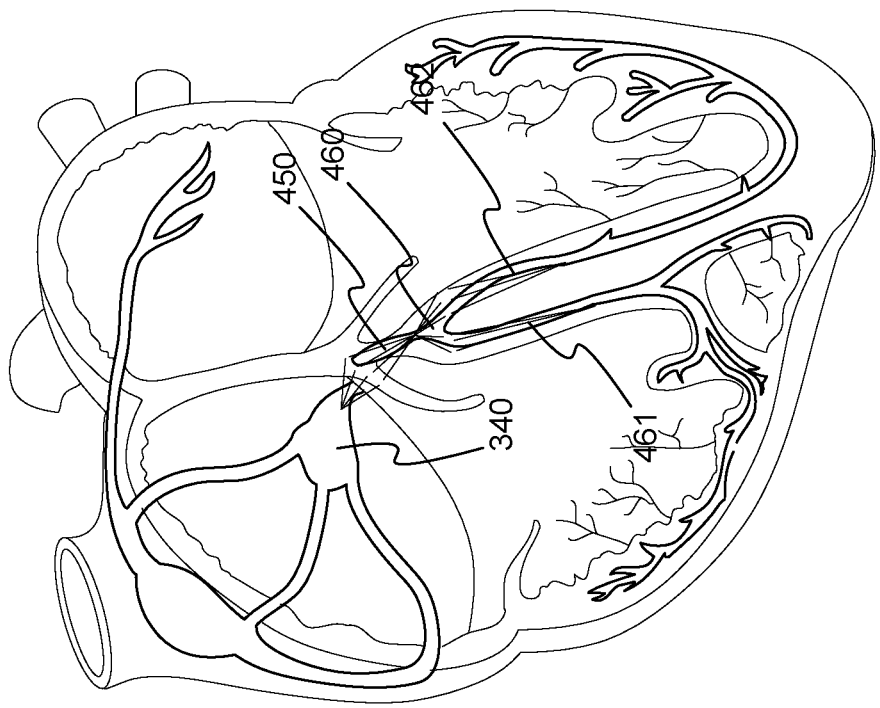
FIG. 4 is an exemplary diagram of the depolarization of the muscle tissue of a heart that produces the PR segment of FIG. 2 as detected by a conventional ECG device.
Figure 5:
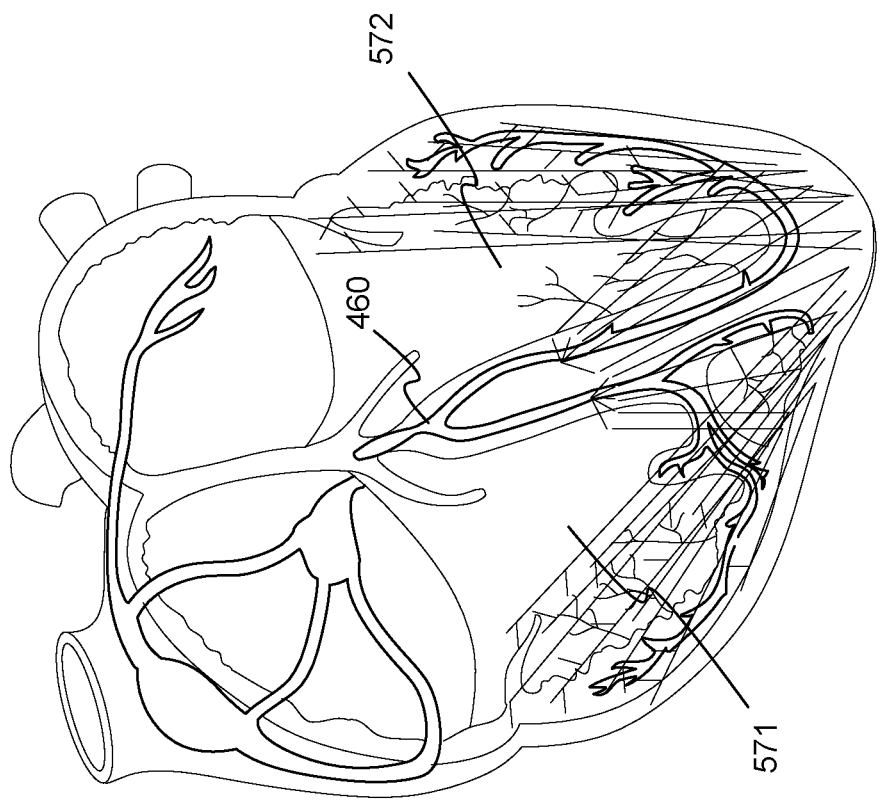
FIG. 5 is an exemplary diagram of the depolarization of the muscle tissue of a heart that produces the Q waveform, the R waveform, and the S waveform of FIG. 2 as detected by a conventional ECG device.
Figure 6:
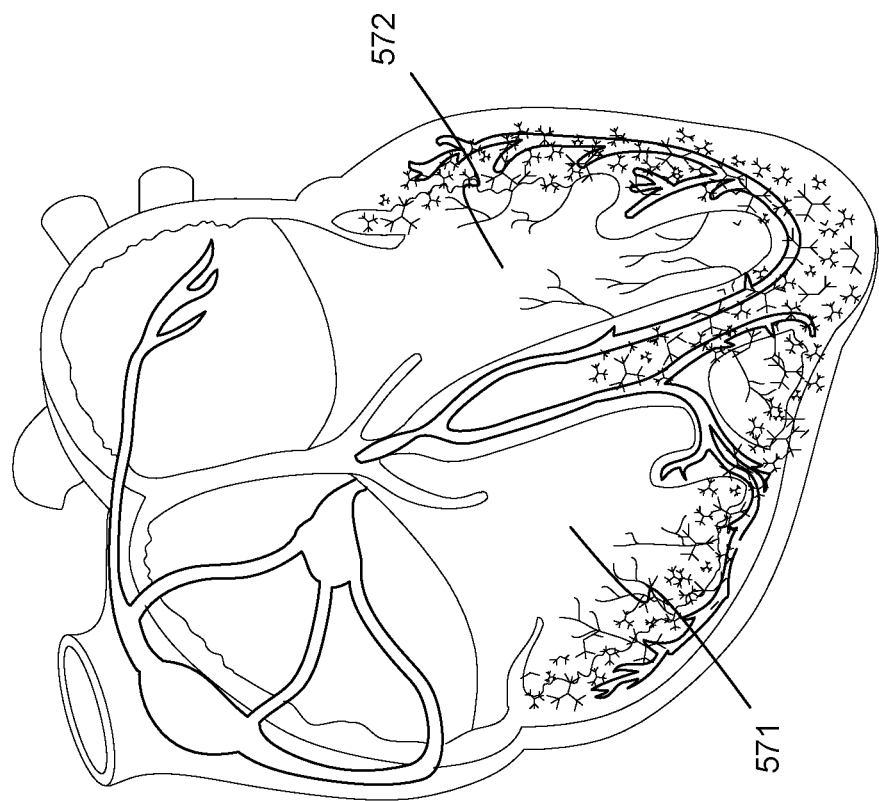
FIG. 6 is an exemplary diagram of the repolarization of the muscle tissue of a heart that produces the T waveform of FIG. 2 as detected by a conventional ECG device.

Display 730 displays a continuous loop of the detected P, Q, R, S, T, U, and J waveforms as shown in FIG. 2 for each pair of electrodes 710. Modern ECG devices can also include a processor (not shown), such as the processor shown in FIG. 1, to analyze the P, Q, R, S, T, U, and J waveforms. For example, the processor can calculate the time periods of the P, Q, R, S, T, U, and J waveforms and the times between the P, Q, R, S, T, U, and J waveforms. The processor can also compare this timing information to stored normal information. Based on the comparison, the processor can determine differences from the normal data. All information calculated by the processor can also be displayed on display 730.

Figure 8:
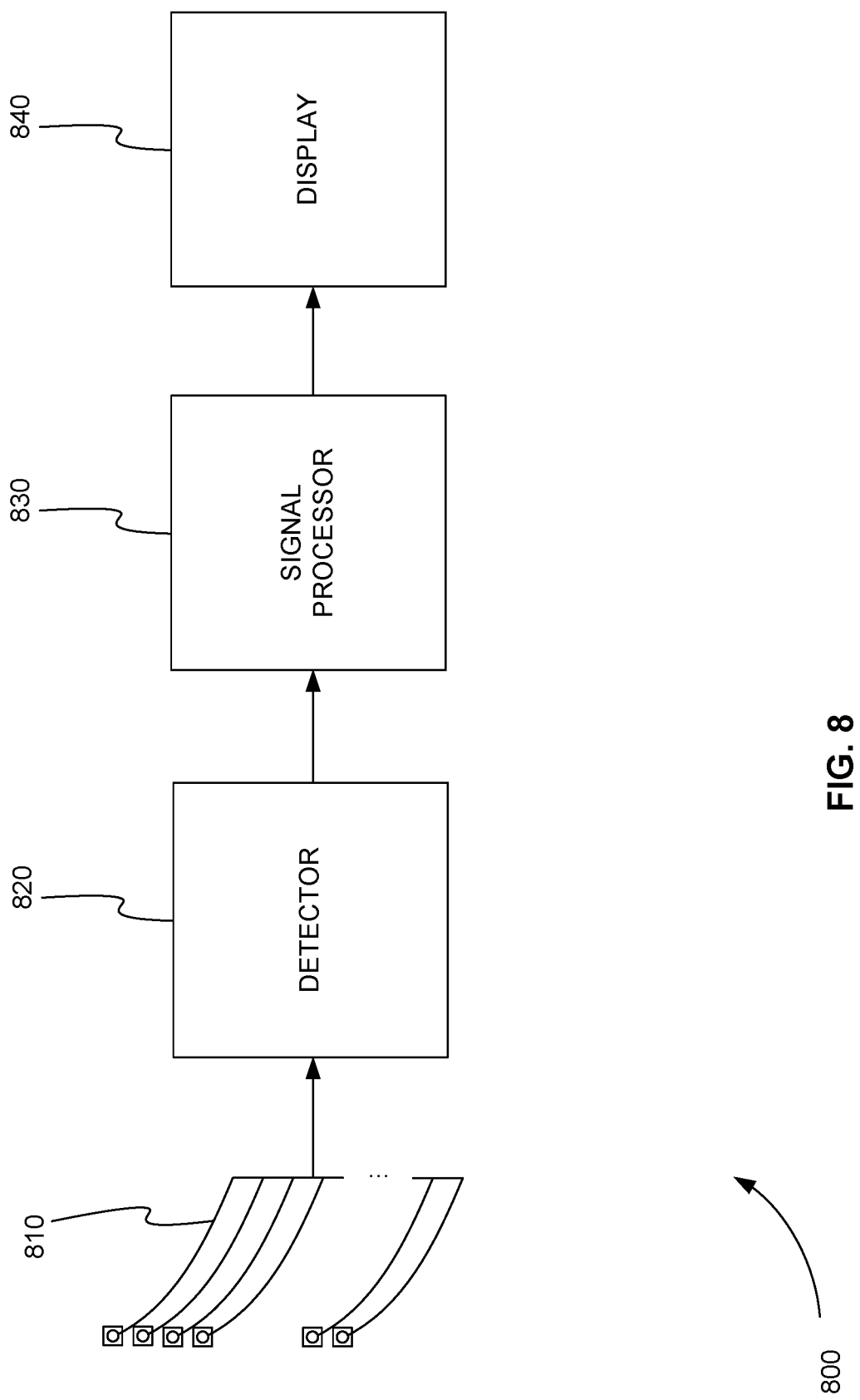
FIG. 8 is a block diagram of an ECG device for detecting more information from the electrical signals that flow through all the different muscle tissues of the heart as it is beating, in accordance with various embodiments.

FIG. 8 is a block diagram 800 of an ECG device for detecting more information from the electrical signals that flow through all the different muscle tissues of the heart as it is beating, in accordance with various embodiments. Electrodes 810 are attached to the skin of a patient, for example. Electrical signals produced by a beating heart are detected between pairs of electrodes 810.

A voltage signal is detected between two electrodes 810 by detector 820. Detector 820 also amplifies the voltage signal. Detector 820 also converts the voltage signal to a digital voltage signal using an analog to digital converter (A/D).

Detector 820 provides the detected and amplified voltage signal from each pair of electrodes 810 to signal processor 830. Detector 820 can also provide the detected and amplified voltage signal from each pair of electrodes 810 directly to display device 840 to display the conventional P, Q, R, S, T, U, and J waveforms.

Signal processor 830 detects or calculates one or more subwaveforms within and/or in the interval between the P, Q, R, S, T, U, and J waveforms of each detected and amplified voltage signal. A waveform is a shape or form of a signal. A subwaveform is shape or form of a signal that is within or part of another signal.

Signal processor 830 can be a separate electronic device that can include, but is not limited to, an application specific integrated circuit (ASIC), a field programmable gate array (FPGA), or a general purpose processor. Signal processor 830 can be software implemented on another processor of the ECG device, such as a processor of display device 840. Signal processor 830 can also be a remote server that receives the detected and amplified voltage signal from detector 820, detects or calculates one or more subwaveforms within and/or in the interval between the P, Q, R, S, T, U, and J waveforms, and sends the detected and amplified voltage signal and the one or more subwaveforms to display device 840.

Signal processor 830 sends one or more subwaveforms of each detected and amplified voltage signal to display device 840. Signal processor 830 can also calculate and send to the display device 840 the time periods of the one or more subwaveforms, the times between the one or more subwaveforms, and the times of the one or more subwaveforms in relation to the P, Q, R, S, T, U, and J waveforms and or the intervals between the P, Q, R, S, T, U, and J waveforms. Signal processor 830 can also compare this timing information to stored normal timing information. Based on the comparison, signal processor 830 can determine differences from the normal data and send this difference information and any of the timing information to display device 840.

Display device 840 displays a continuous loop of the one or more subwaveforms for each pair of electrodes 810. Display device 840 can also display part or all of the conventional P, Q, R, S, T, U, and J waveforms for comparison with the one or more subwaveforms. Like display 730 of FIG. 7, display device 840 of FIG. 8 can be an electronic display device, a printer, or any combination of the two.

In various embodiments, an ECG device using signal processing to detect one or more subwaveforms within the P, Q, R, S, T, U, and J waveforms and/or within the intervals between the P, Q, R, S, T, U, and J waveforms is herein referred to as a saah ECG device. The voltage difference signals produced by a saah ECG device are referred to as saah ECG waveforms. The term "saah" is an acronym for some of the anatomically distinct portions of muscle tissue that produce subwaveforms. Specifically, saah stands for sinoatrial node (SAN), atria (right atrium (RA) and left atrium (LA)), atrioventricular node (AVN), and bundle of His (HIS). However, a saah ECG waveform is not limited to including subwaveforms representing the SAN, the atria, the AVN, and the HIS. A saah ECG waveform can include any subwaveform the P, Q, R, S, T, U, and J waveforms and/or within the intervals between the P, Q, R, S, T, U, and J waveforms.

Figure 9:
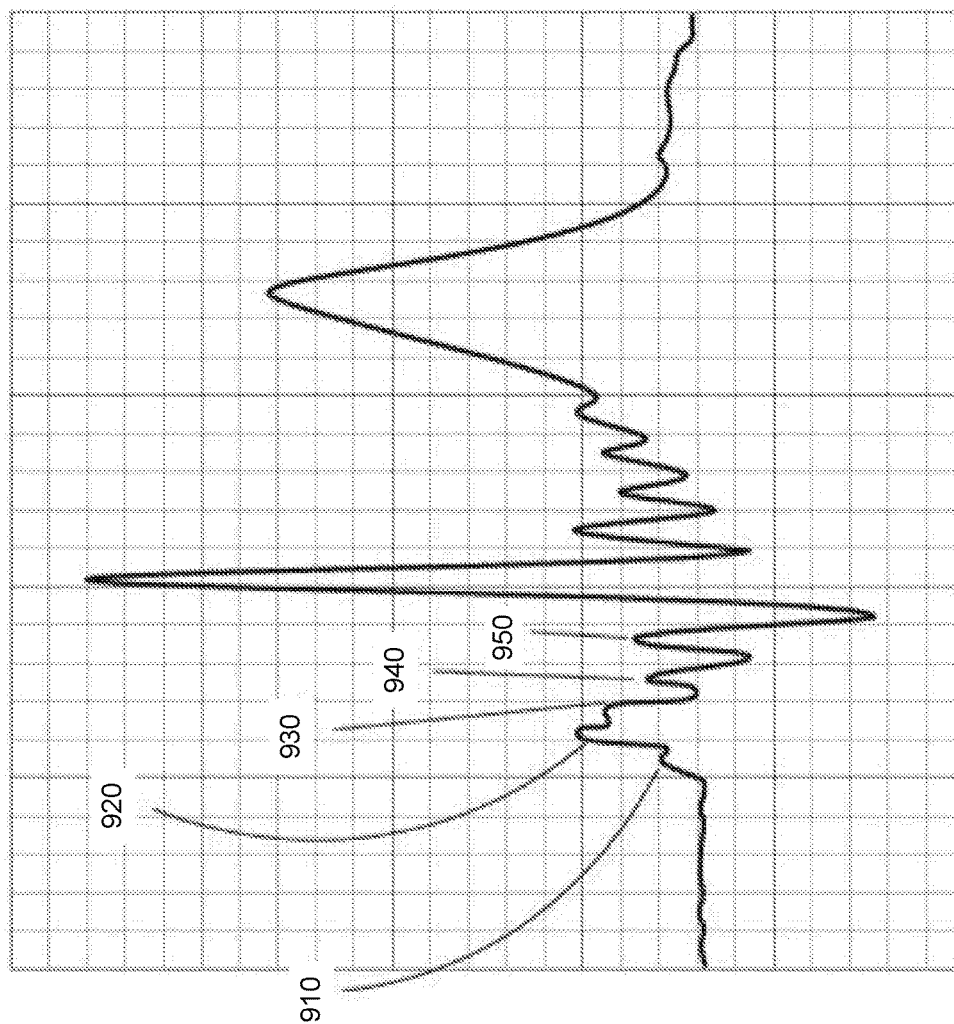
FIG. 9 is an exemplary plot of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments.

FIG. 9 is an exemplary plot 900 of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments. For example, five subwaveforms 910-950 of FIG. 9 are detected within the P waveform and the PR segment. The time period that includes the P waveform and the PR segment is also called the PR interval. Subwaveform 910 represents the depolarization of the SAN. Subwaveform 920 represents the depolarization of RA and LA. Subwaveform 930 represents the depolarization of the AVN. Subwaveform 940 represents the depolarization HIS. Finally, subwaveform 950 represents the depolarization of the bundle branches (BB).

In various embodiments, the subwaveforms of a saah ECG waveform are detected using signal processing. Electrodes 810 of the saah ECG of FIG. 8, for example, receive electrical impulses from anatomically distinct portions of muscle tissue or cells. The electrical impulses of anatomically distinct portions of muscle tissue of the heart have distinct frequencies. Through animal and human experimentation, the distinct frequency, frequency range, or frequency band of the anatomically distinct portions of muscle tissue of the heart are found. These distinct frequency bands of anatomically distinct portions of muscle tissue of the heart provide predetermined data or information for signal processing. In other words, the band pass frequency filtering of the signal processing is determined from the experimental data collected. A saah ECG device then employs one or more frequency band pass filters to detect the one or more subwaveforms.

Figure 10:
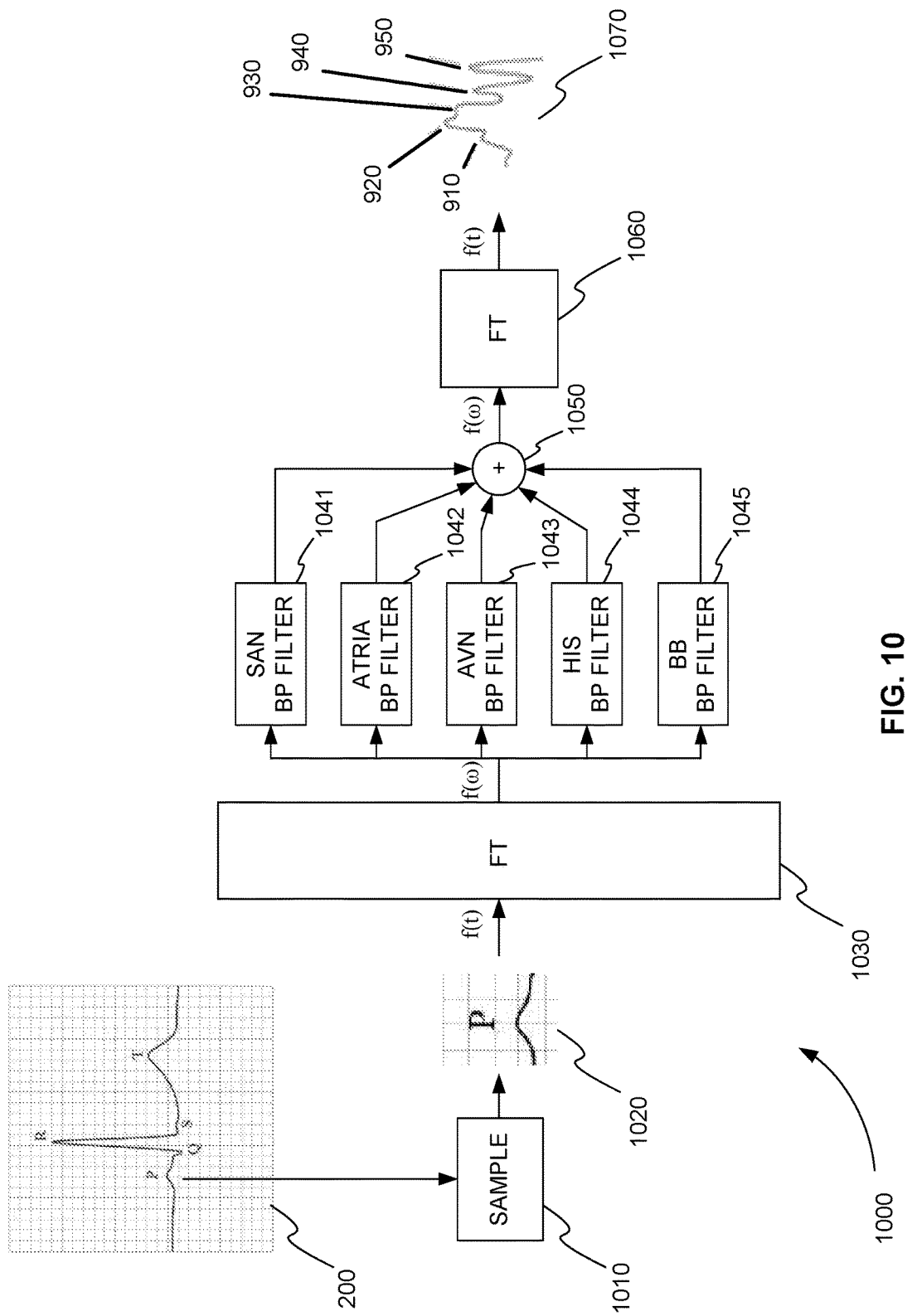
FIG. 10 is an exemplary block diagram showing a signal processing algorithm for detecting five subwaveforms within the PR interval of a conventional ECG waveform, in accordance with various embodiments.

FIG. 10 is an exemplary block diagram 1000 showing a signal processing algorithm for detecting five subwaveforms within the PR interval of a conventional ECG waveform, in accordance with various embodiments. Sampling block 1010 samples the electrical impulses in the PR interval time period of each heart. This is shown graphically in FIG. 1000 by separating PR interval 1020 from ECG waveform 200. The electrical impulses in the PR interval time period are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 10, block 1030 converts the PR interval time domain signal to a PR interval frequency domain signal. The time domain signal is converted into a frequency domain signal using a Fourier transform, for example.

As described above, through animal and/or human experimentation, the frequency bands associated with depolarization of the SAN, atria, AVN, HIS, and BB of the heart are determined. Based on these frequency bands, band pass filters are created. Blocks 1041-1045 represent the band pass filters created to filter the PR interval frequency domain signal for frequency bands of the SAN, atria, AVN, HIS, and BB of the heart, respectively.

In block 1050, the frequency domain subwaveforms detected from the band pass filtering the frequency bands of the SAN, atria, AVN, HIS, and BB of the heart are summed. In block 1060, the filtered and summed frequency domain signal of the PR interval is converted back to a time domain signal. The frequency domain signal is converted into a time domain signal using a Fourier transform, for example.

The PR interval filtered and summed time domain signal 1070 includes five time domain subwaveforms 910-950. Subwaveforms 910-950 represent depolarization of the SAN, atria, AVN, HIS, and BB of the heart, respectively. Time domain signal 1070 can be used to replace PR interval 1020 in ECG waveform 200, for example. As a result, a saah ECG waveform is produced.

FIG. 10 shows a signal processing algorithm for detecting five subwaveforms. However, similar steps can be applied to detect fewer than five waveforms or more than five waveforms. Also, the steps of FIG. 10 describe detecting subwaveforms within the PR interval. However, similar steps can be applied to detect subwaveforms within the P, Q, R, S, T, U, and J waveforms and/or within one or more of the intervals between the P, Q, R, S, T, U, and J waveforms. In addition, the steps of FIG. 10 describe converting time signals to the frequency domain and then back to the time domain. One of ordinary skill in the art can appreciate that band pass filters can be applied directly to the time domain signal to provide the same result.

Figure 11:
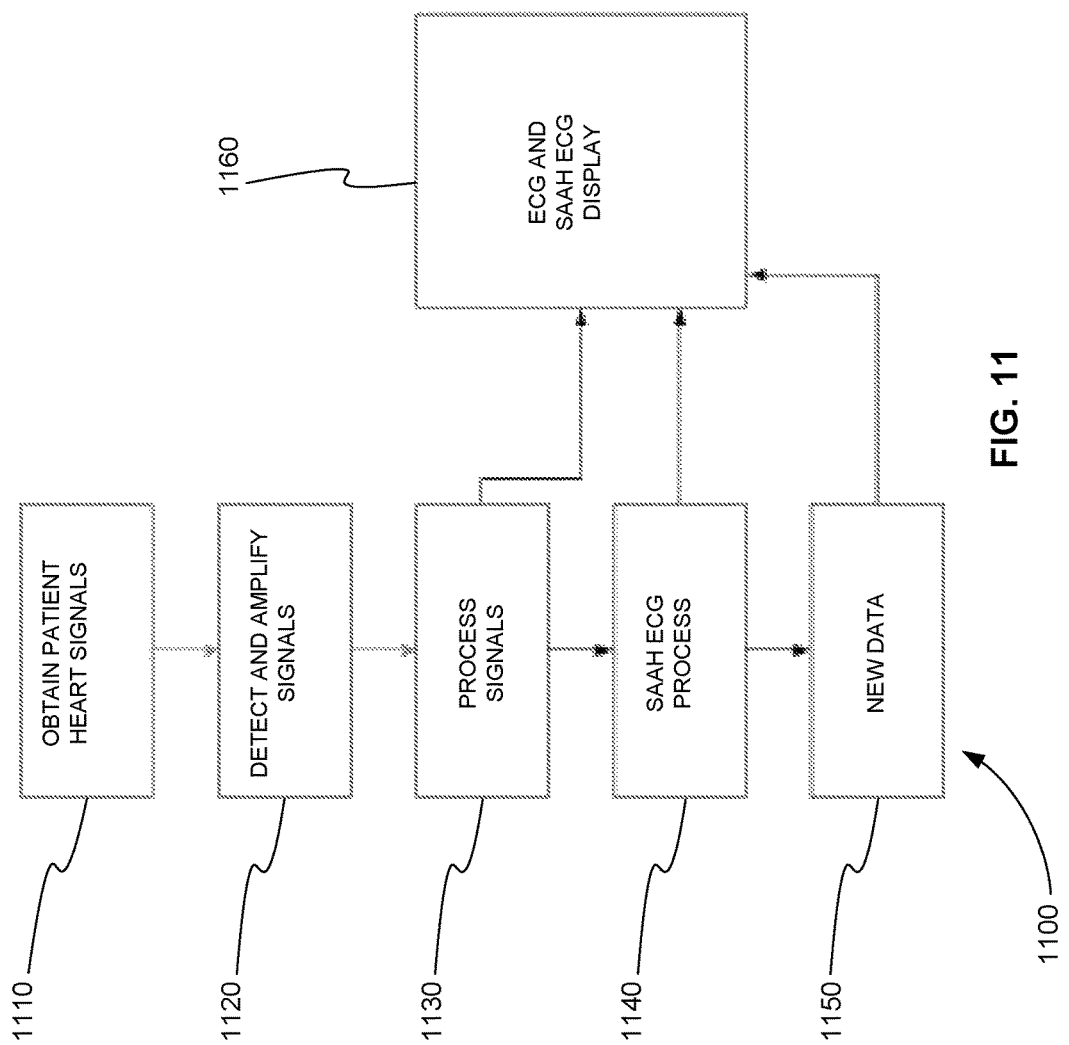
FIG. 11 is an exemplary block diagram of a saah ECG device that displays conventional ECG waveforms, saah ECG waveforms, and saah ECG data, in accordance with various embodiments.

FIG. 11 is an exemplary block diagram 1100 of a saah ECG device that displays conventional ECG waveforms, saah ECG waveforms, and saah ECG data, in accordance with various embodiments. In block 1110, patient heart signals are obtained. These heart signals can be obtained through noninvasive electrodes placed on the skin, such as electrodes 810 show in FIG. 8. In various embodiments, heart signals may also be obtained using invasive electrodes placed directly on the heart. In block 1120, the heart signals are detected using a detector and amplified.

In block 1130, the detected and amplified heart signals are processed using a signal processor. The signal processor detects the conventional P, Q, R, S, T, U, and J waveforms and sends them to the display of block 1160. The signal processor also detects or calculates subwaveforms within the conventional P, Q, R, S, T, U, and J waveforms and/or within intervals between the conventional P, Q, R, S, T, U, and J waveforms. The signal processor sends the subwaveforms to block 1140 for further processing. The processor of block 1140 produces the saah ECG waveform that includes the subwaveforms and sends the saah ECG waveform to the display of block 1160. The processor of block 1140 calculates additional information or new data from the saah ECG waveform. This new data can include, but is not limited to, timing information about the subwaveforms, timing information about the intervals between the subwaveforms, and timing information about the subwaveforms and their relation to the conventional P, Q, R, S, T, U, and J waveforms. In block 1150, this new data is sent to the display of block 1160.

The display of block 1160 displays a continuous loop of the conventional ECG waveform, the saah ECG waveform, and the new data from the subwaveforms. The display of block 1160 can display this information on an electronic display or print it on paper. The display of block 1160 can also record this information. The display of block 1160 can record this information on any type of memory device.

Figure 12:
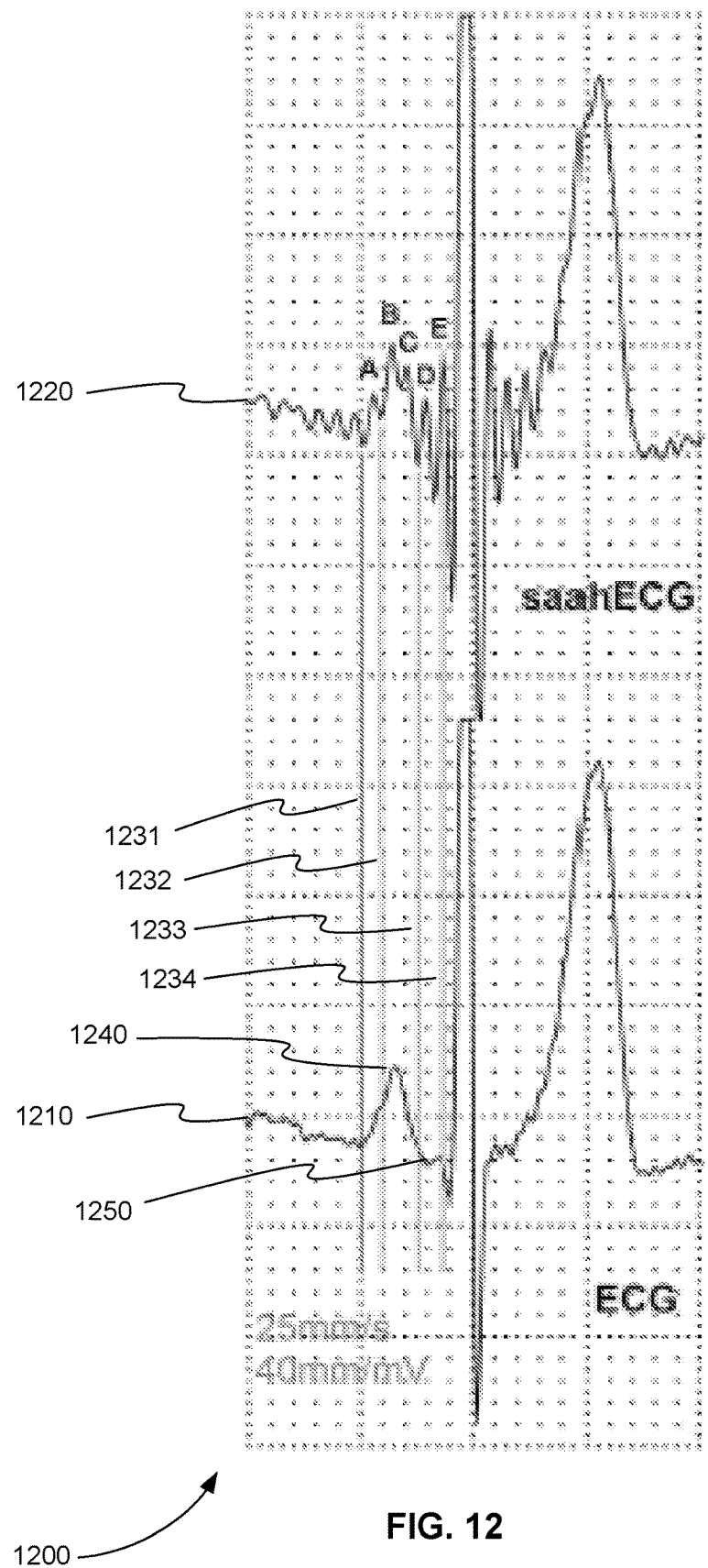
FIG. 12 is an exemplary plot of the information displayed by the saah ECG device of FIG. 10, in accordance with various embodiments.

FIG. 12 is an exemplary plot 1200 of the information displayed by the saah ECG device of FIG. 11, in accordance with various embodiments. Plot 1200 includes conventional ECG waveform 1210 and saah ECG waveform 1220. Saah ECG waveform 1220, for example, includes, among others, five subwaveforms A-E representing the depolarization of the SAN, the RA and LA, the AVN, the HIS, and the BB, respectively.

Plot 1200 also shows new data or timing information about the subwaveforms and their relation to the conventional P, Q, R, S, T, U, and J waveforms. For example, the time interval between line 1231 and line 1232 relates subwaveform A of saah ECG waveform 1220 to P waveform 1240 of conventional ECG waveform 1210. The time interval between line 1232 and line 1233 relates subwaveforms B and C of saah ECG waveform 1220 to P waveform 1240 conventional ECG waveform 1210. The time interval between line 1233 and line 1234 relates subwaveforms D and E of saah ECG waveform 1220 to PR segment 1250 conventional ECG waveform 1210.

Figure 13:
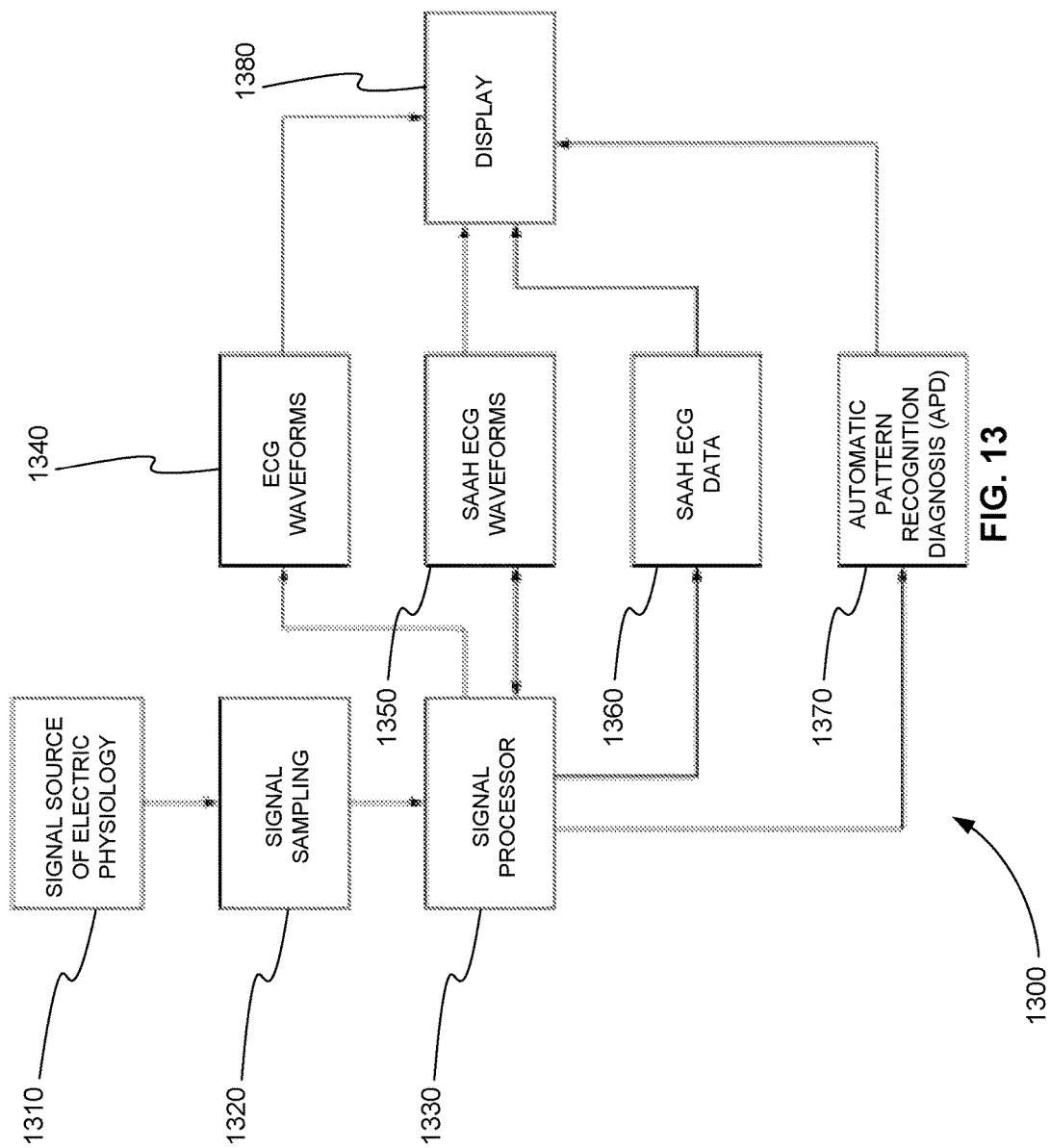
FIG. 13 is an exemplary block diagram of a saah ECG device that displays conventional ECG waveforms, saah ECG waveforms, saah ECG data, and saah ECG automatic pattern recognition diagnosis information, in accordance with various embodiments.

FIG. 13 is an exemplary block diagram 1300 of a saah ECG device that displays conventional ECG waveforms, saah ECG waveforms, saah ECG data, and saah ECG automatic pattern recognition diagnosis information, in accordance with various embodiments. In block 1310, patient heart signals are obtained. These heart signals can be obtained through noninvasive electrodes placed on the skin, such as electrodes 810 show in FIG. 8. In various embodiments, heart signals may also be obtained using invasive electrodes placed directly on the heart. In block 1320, the heart signals are sampled or detected using a detector. The heart signals may also be amplified.

In block 1330, the sampled heart signals are processed using a signal processor. The signal processor produces four different types of information from the sampled heart signals. As shown in block 1340, the signal processor produces conventional ECG waveforms including the conventional P, Q, R, S, T, U, and J waveforms and sends them to display 1380. As shown in block 1350, the signal processor produces saah ECG waveforms. These saah ECG waveforms include subwaveforms of the conventional P, Q, R, S, T, U, and J waveforms and the intervals between them. Note that the arrow between blocks 1330 and 1350 show information following in both directions. This shows that information from the saah ECG waveforms is further analyzed by the signal processor.

As shown in block 1360, the signal processor further analyzes the saah ECG waveforms to produce saah ECG data. This saah ECG data is sent to display 1380. Additionally, as shown in block 1370, the signal processor further analyzes the saah to obtain endocardium and epicardium data. This data is compared to recorded normal and abnormal data. The signal processor then produces automatic pattern recognition diagnosis (APD) information, and this information is sent to display 1380. APD information is, for example, patterns and/or colors that allow a user to easily and quickly determine that normal or abnormal endocardium and/or epicardium data was found.

Figure 14:
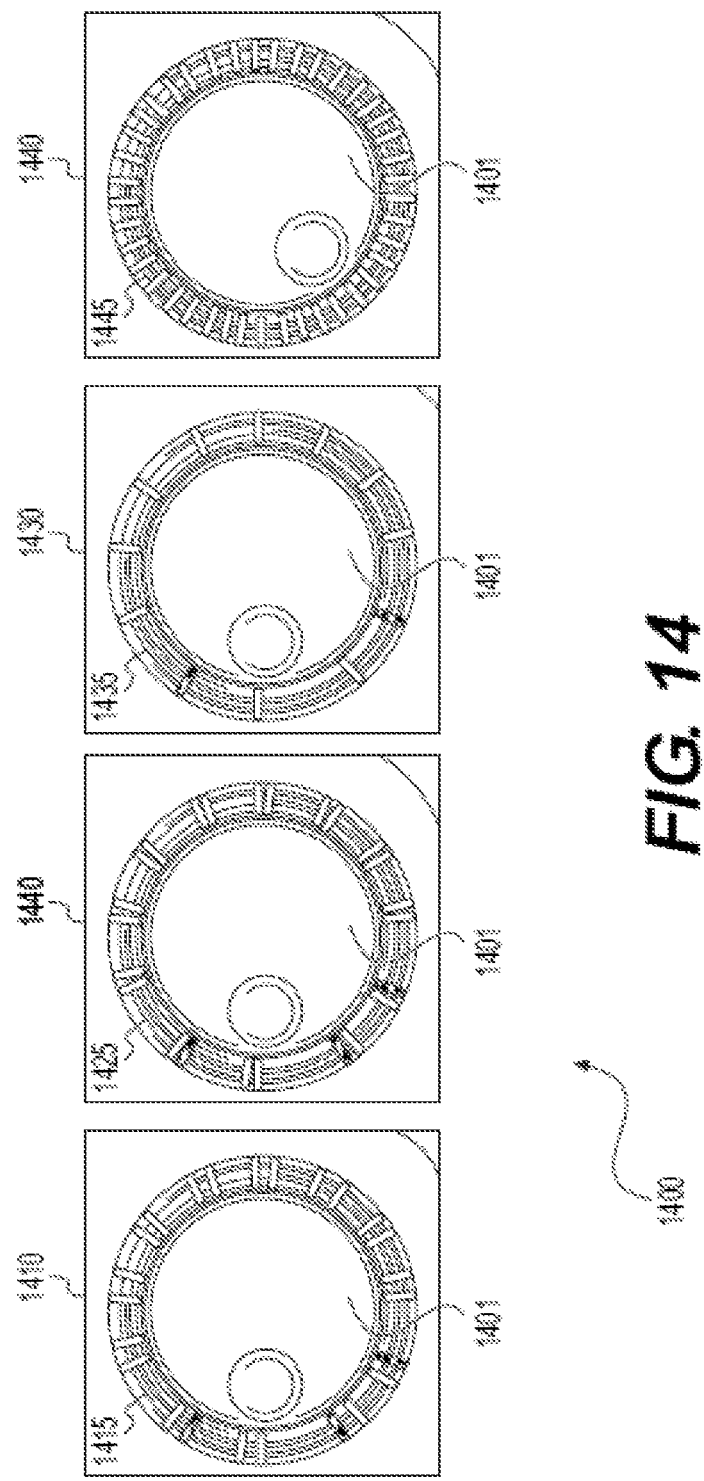
FIG. 14 is a series of photographs of automatic pattern recognition diagnosis (APD) information displayed around a rotating button of an exemplary saah ECG device, in accordance with various embodiments.

FIG. 14 is a series 1400 of photographs of automatic pattern recognition diagnosis (APD) information displayed around a rotating button of an exemplary saah ECG device, in accordance with various embodiments. Photograph 1410 shows information 1415 displayed around rotating button 1401. Information 1415 includes a pattern and colors that indicate a normal state of the saah ECG waveforms. Photograph 1420 shows information 1425 displayed around rotating button 1401. Information 1425 includes a pattern and colors that indicate a suspicious state of the saah ECG waveforms. Photograph 1430 shows information 1435 displayed around rotating button 1401. Information 1435 includes a pattern and colors that indicate an abnormal state of the saah ECG waveforms. Photograph 1440 shows information 1445 displayed around rotating button 1401. Information 1445 includes a pattern and colors that indicate an invalid result in the saah ECG waveforms.

In various embodiments, the additional information provided by a saah ECG device can be used to diagnose heart problems that cannot be diagnosed using conventional ECG devices or cannot easily be diagnosed using conventional ECG devices. The additional information provided by a saah ECG device can also be used in the treatment of heart problems or the assessment of these treatments.

Figure 15:
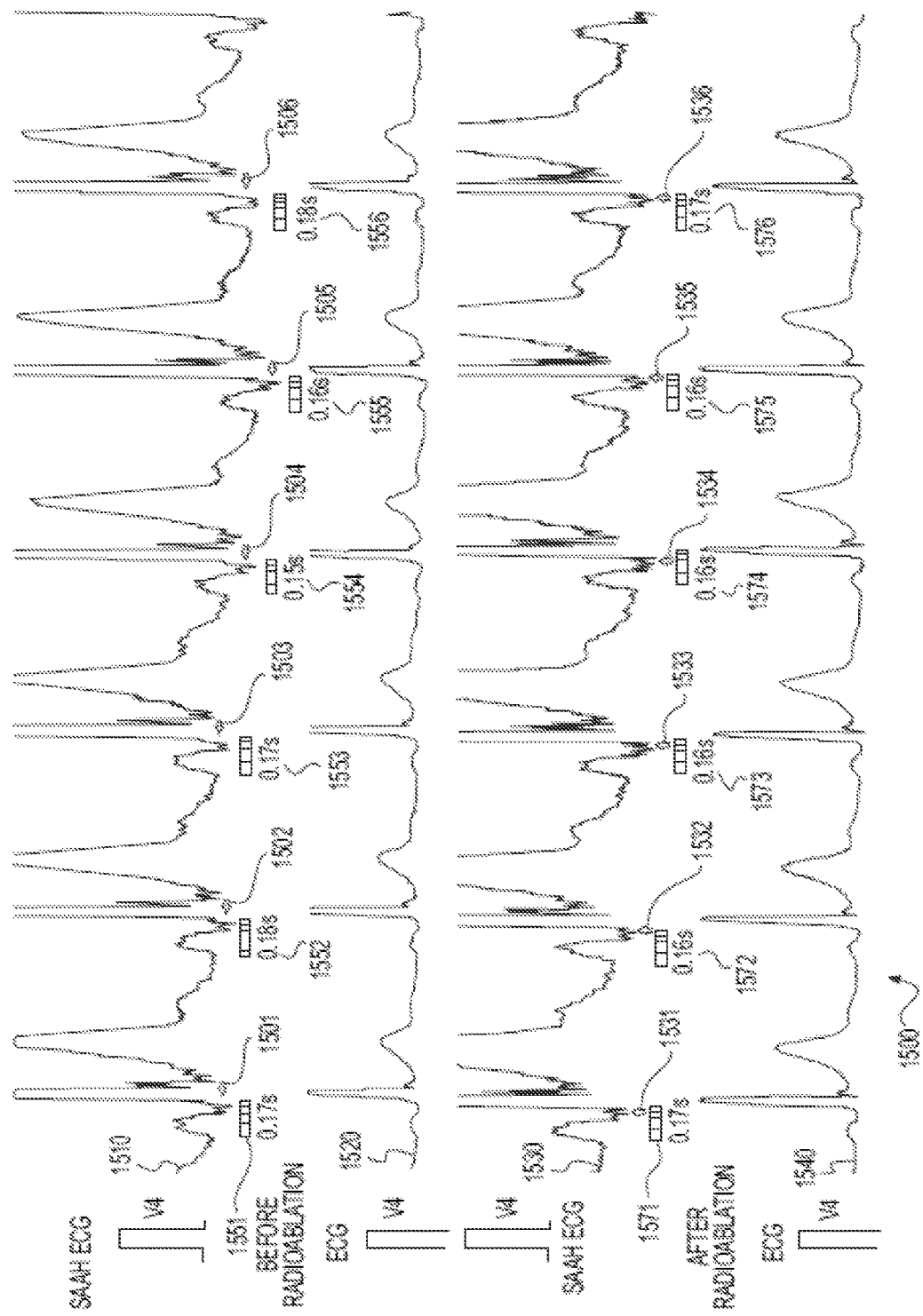
FIG. 15 is a plot of saah ECG and conventional ECG waveforms taken from a patient suffering from Wolff-Parkinson-White (WPW) syndrome before and after treatment with radiofrequency ablation (RFA) showing the additional diagnostic and treatment assessment information provided by a saah ECG device, in accordance with various embodiments.

FIG. 15 is a plot 1500 of saah ECG and conventional ECG waveforms taken from a patient suffering from Wolff-Parkinson-White (WPW) syndrome before and after treatment with radiofrequency ablation (RFA) showing the additional diagnostic and treatment assessment information provided by a saah ECG device, in accordance with various embodiments. WPW syndrome is caused by the presence of abnormal electrical pathways in the heart muscle tissue. There are, at least, three different types of abnormal pathways. These abnormal pathways cause cardiac tachycardia. Cardiac tachycardia is an abnormally rapid heart rate.

Plot 1500 shows before saah ECG waveform 1510, before conventional ECG waveform 1520, after saah ECG waveform 1530, and after conventional ECG waveform 1540. Waveforms 1510, 1520, 1530, and 1540 are produced for example using a saah ECG device. A saah ECG device also produces conventional ECG waveforms for comparison with the saah ECH waveforms. Waveforms 1510, 1520, 1530, and 1540 are produced using a $V_4$ electrode, for example. A $V_4$ electrode is placed in the fifth intercostal space (between ribs 5 and 6) in the mid-clavicular line, for example.

As described above, saah ECG waveforms show subwaveforms of the conventional P, Q, R, S, T, U, and J waveforms and the intervals between them. These subwaveforms provide more information on the function of specific and anatomically distinct portions of the muscle tissue of the heart.

For example, arrows 1503 and 1506 point to areas of two beats of before saah ECG waveform 1510 where the subwaveform showing the depolarization of the bundle branches (BB) is missing. Arrows 1501, 1502, 1504, and 1505 point to areas of four beats where the subwaveform showing the depolarization of the BB appears as half of the normal subwaveform. As a result, in two of the six beats of before ECG waveform 1510 the subwaveform representing the BB is missing, and in four of the six beats of before saah ECG waveform 1510 the subwaveform representing the BB is abnormal. A normal subwaveform representing the BB has a shape, for example, like subwaveform 950 of FIG. 9.

This information from before saah ECG waveform 1510 of FIG. 15 regarding the BB can be used to diagnose the specific abnormal pathway present in this case of WPW syndrome. Further, this information can be used to determine the treatment. In contrast, none of this information can be obtained from before conventional ECG waveform 1520.

In addition to providing a saah ECG waveform, a saah ECG device can provide additional data regarding the subwaveforms found. For example, plot 1500 includes subwaveform timing information for the PR interval of each heartbeat. This timing information is provided as timing diagrams 1551-1556 for the six heartbeats. Each timing diagram provides a numeral value for the period of the PR interval and a horizontal stacked bar graph depicting how four time intervals containing one or more subwaveforms are distributed with PR interval time period. The horizontal stacked bar graphs can include different colors, patterns, or shades, for example.

The first interval of each horizontal stacked bar graph is the interval that includes the subwaveform representing the depolarization of the sinoatrial node (SAN). The second interval is the interval that includes the subwaveforms representing the depolarization of the atria (right atrium (RA) and left atrium (LA)) and the atrioventricular node (AVN). The third interval is the interval that includes the subwaveform representing the depolarization of the bundle of His (HIS) of the beating heart. The fourth interval is the interval that includes the subwaveform representing the depolarization of the bundle branches (BB).

A comparison of the horizontal stacked bar graphs of timing diagrams 1551-1556 shows that the periods of the four intervals vary widely over the six heartbeats. This is also an indication of the underlying disease. This timing information is not available in before conventional ECG waveform 1520.

RFA was performed on the patient presenting before saah ECG waveform 1510 and before conventional ECG waveform 1520. A muscular conduction bridge connecting the right atrium and the right ventricle (bundle of Kent) and a connections between the A-V bundle and the interventricular septum (Mahaim's connections) were ablated, for example.

After treatment with RFA, the patient's return to a normal heartbeat can be confirmed with after saah ECG waveform 1530. For example, arrows 1531-1536 of the six heartbeats shown in after saah ECG waveform 1530 point to areas that show that the subwaveform of the BB has returned in all six heartbeats after treatment. In contrast, after treatment conventional ECG waveform 1540 cannot provide this information.

In addition, a comparison of the horizontal stacked bar graphs of timing diagrams 1571-1576 for after saah ECG waveform 1530 shows that the periods of the four intervals of the PR interval do not vary widely over the six heartbeats. This is also an indication of the effectiveness of the RFA treatment. This timing information is not available in after conventional ECG waveform 1540.

System for Detecting ECG Subwaveforms

In various embodiments, an electrocardiography (ECG) system for detecting one or more subwaveforms within the P, Q, R, S, T, U, and J waveforms or in an interval between the P, Q, R, S, T, U, and J waveforms is provided. Returning to FIG. 8, the ECG system includes two or more electrodes 810, a detector 820, a signal processor 830, and a display device 840.

Two or more electrodes 810 are placed near a beating heart and receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses. In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor 830 receives the ECG waveform from detector 820. Signal processor 830 detects or calculates one or more subwaveforms within P, Q, R, S, T, U, and J waveforms of the ECG waveform or in an interval between the P, Q, R, S, T, U, and J waveforms that represent the depolarization or repolarization of anatomically distinct portions of muscle tissue of the beating heart. Signal processor 830 produces a processed ECG waveform that includes the one or more subwaveforms for each heartbeat.

Signal processor 830 can be a separate device, can be software running on a device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general purpose processor. A general purpose processor can include, but is not limited to, a microprocessor, a microcontroller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820, detects or calculates one or more subwaveforms within and/or in the interval between the P, Q, R, S, T, U, and J waveforms, and sends the detected and amplified different voltage signal and the one or more subwaveforms to display device 840.

Display device 840 receives the processed ECG waveform for each heartbeat and displays the processed ECG waveform for each heartbeat. The processed ECG waveform is called a saah ECG waveform, for example. As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record saah ECG waveforms, saah ECG data and conventional ECG waveforms and data. The memory device can be, but is not limited to, a volatile electronic memory, such as random access memory (RAM), a non-volatile electronic memory, such as electrically erasable programmable read-only memory (EEPROM or Flash memory), or a magnetic hard drive.

In various embodiments, the detected one or more subwaveforms include at least one subwaveform representing depolarization of the sinoatrial node (SAN), the atria (right atrium (RA) and left atrium (LA)), the atrioventricular node (AVN), the bundle of His (HIS), or the bundle branches (BB) of the beating heart.

In various embodiments, the display device 840 further displays the ECG waveform for comparison with the processed ECG waveform.

In various embodiments, signal processor 830 further calculates timing information about the one or more subwaveforms, timing information about the intervals between the one or more subwaveforms, and timing information about the one or more subwaveforms and their relation to the P, Q, R, S, T, U, and J waveforms of the ECG waveform for each heartbeat. Display device 840 further receives this timing information from signal processor 830. Display device 840 displays the timing information about the one or more subwaveforms, the timing information about the intervals between the one or more subwaveforms, and the timing information about the one or more subwaveforms and their relation to the P, Q, R, S, T, U, and J waveforms of the ECG waveform for each heartbeat.

In various embodiments, the ECG system further includes a memory device (not shown). The memory device receives the ECG waveform and the processed ECG waveform from the signal processor.

In various embodiments, the memory device further includes normally processed ECG waveform data. Normally processed ECG waveform data is stored on the memory device using signal processor 830 or a general-purpose processor (not shown). Signal processor 830 further compares the processed ECG waveform to the normally processed ECG waveform data and calculates a status condition based on the comparison. The status conditions are, for example, normal, suspicious, or abnormal.

In various embodiments, the ECG system includes a second display device (not shown) surrounding a rotating button (not shown). Signal processor 830 further sends a colored pattern to the second display device based on the status condition. The second display device provides automatic pattern recognition diagnosis (APD).

Method for Detecting ECG Subwaveforms

Figure 16:
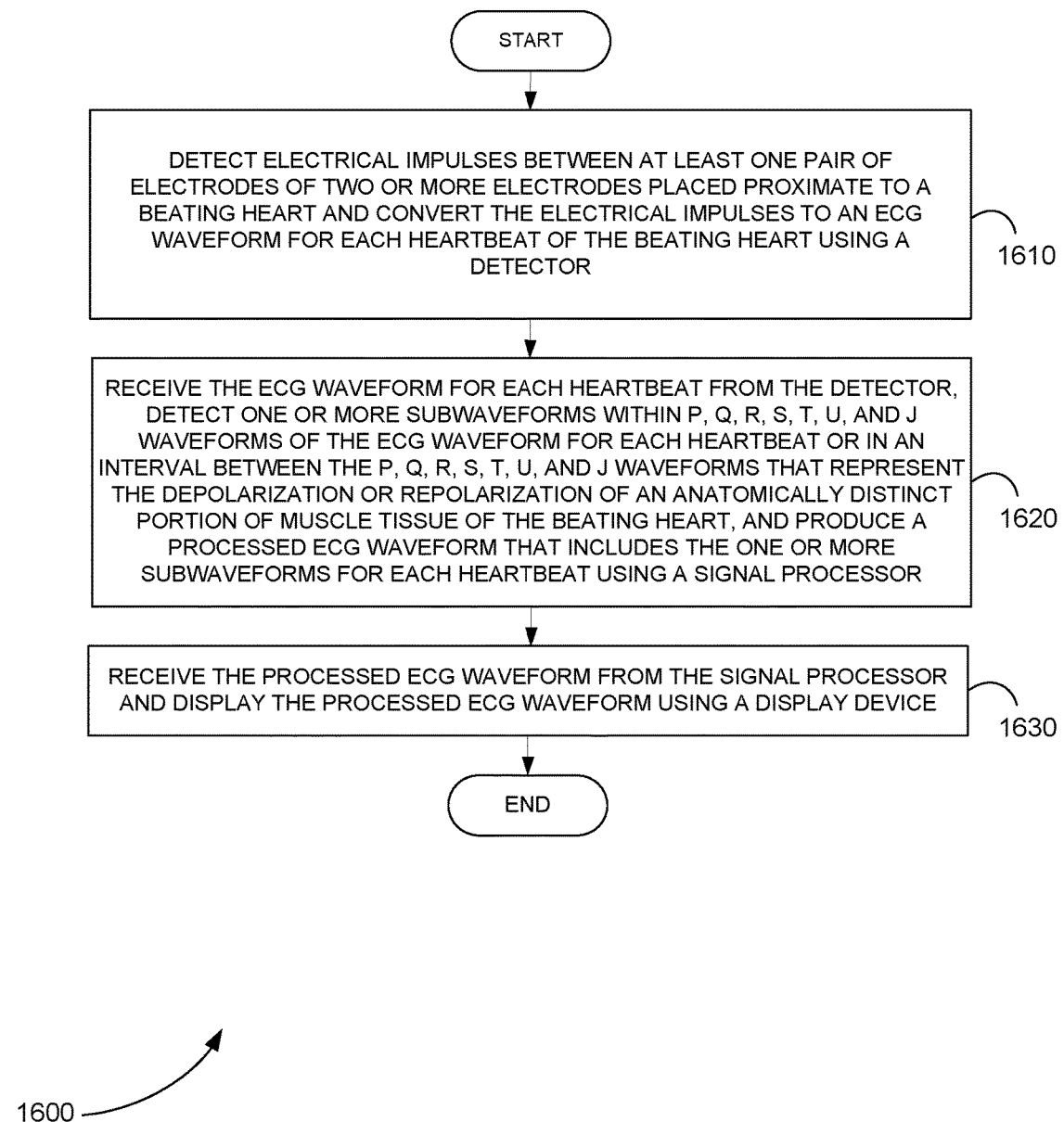
FIG. 16 is a flowchart showing a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 16 is a flowchart showing a method 1600 for detecting subwaveforms within the P, Q, R, S, T, U, and J waveforms of an ECG waveform of a heartbeat or in an interval between the P, Q, R, S, T, U, and J waveforms, in accordance with various embodiments.

In step 1610 of method 1600, electrical impulses are detected between at least one pair of electrodes of two or more electrodes placed proximate to a beating heart using a detector. The electrical impulses are converted to an ECG waveform for each heartbeat of the beating heart using the detector.

In step 1620, the ECG waveform for each heartbeat is received from the detector using a signal processor. One or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart are detected using the signal processor. A processed ECG waveform that includes the one or more subwaveforms for each heartbeat is produced using the signal processor.

In step 1630, the processed ECG waveform is received from the signal processor and the processed ECG waveform is displayed using a display device.

Computer Program Product for Detecting ECG Subwaveforms

In various embodiments, computer program products include a tangible computer-readable storage medium whose contents include a program with instructions being executed on a processor so as to perform a method for detecting subwaveforms within the P, Q, R, S, T, U, and J waveforms of an ECG waveform of a heartbeat or in an interval between the P, Q, R, S, T, U, and J waveforms. This method is performed by a system that includes one or more distinct software modules.

Figure 17:
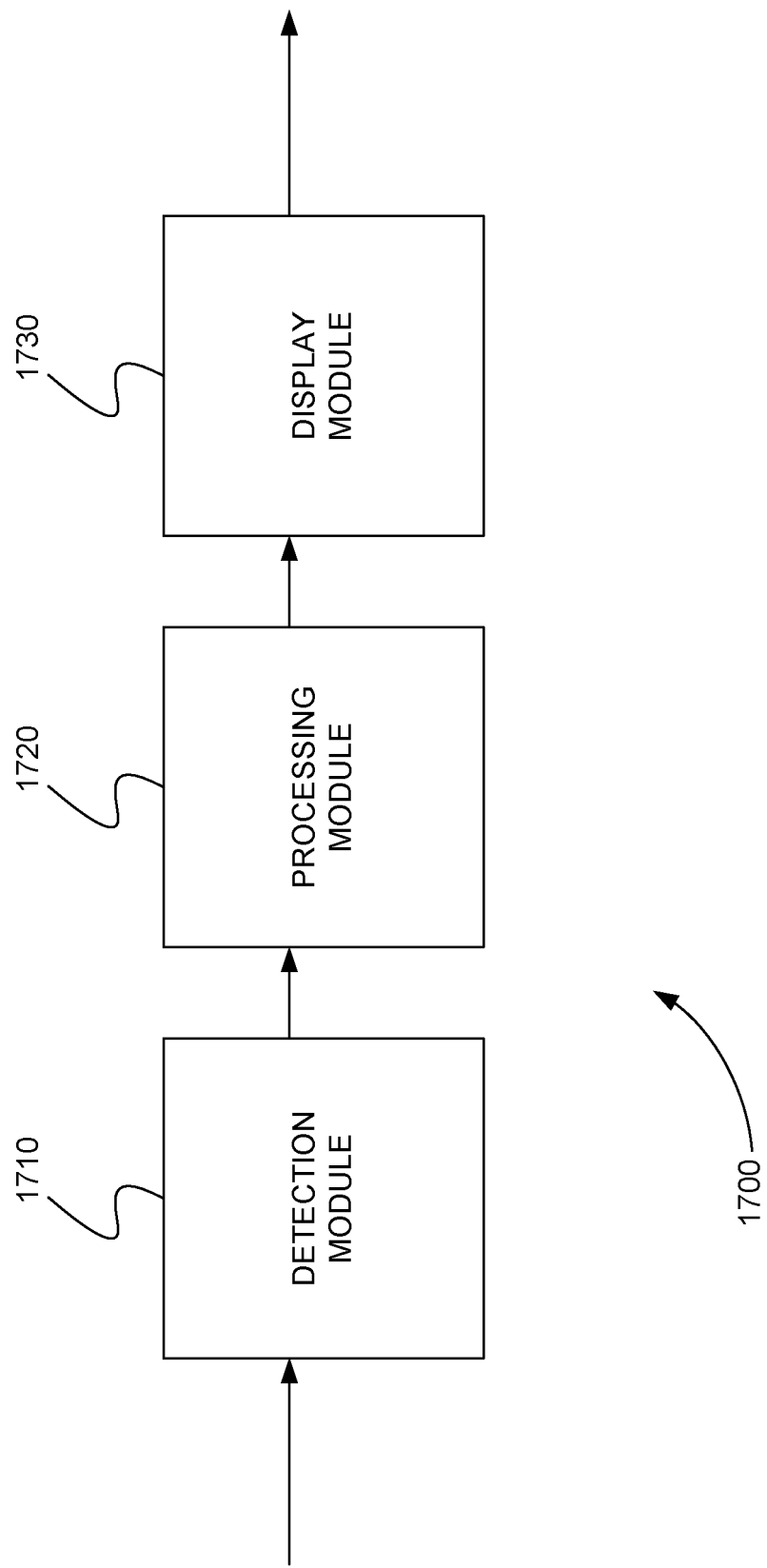
FIG. 17 is a schematic diagram of a system that includes one or more distinct software modules that performs a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 17 is a schematic diagram of a system 1700 that includes one or more distinct software modules that performs a method for detecting subwaveforms within the P, Q, R, S, T, U, and J waveforms of an ECG waveform of a heartbeat or in an interval between the P, Q, R, S, T, U, and J waveforms, in accordance with various embodiments. System 1700 includes detection module 1710, processing module 1720, and display module 1730.

Detection module 1710 detects electrical impulses between at least one pair of electrodes of two or more electrodes placed proximate to a beating heart. Detection module 1710 converts the electrical impulses to an ECG waveform for each heartbeat of the beating heart.

Processing module 1720 receives the ECG waveform for each heartbeat. Processing module 1720 detects one or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart. Processing module 1720 produces a processed ECG waveform that includes the one or more subwaveforms for each heartbeat.

Display module 1730 receives the processed ECG waveform. Display module 1730 displays the processed ECG waveform.

Multi-Domain ECG

The heart muscle, like other muscles, is activated by biologically generated electrical signals. Electrocardiography (ECG or EKG) has long been used to measure and record these electrical signals. Essentially, in ECG the electrical activity of the heart is measured from a number of different points on the body and plotted over time. As a result, ECG traces out each cardiac cycle or heartbeat as a voltage versus time waveform.

A human heart has two functional systems. The first system, referred to as a self-conduction system, is part of the atrium (including left and right atria). In a traditional ECG, the self-conduction system is represented by the P wave or PR interval. The excitation, rhythm, and conduction of every beat is completed by the collaboration of all parts of the heart, which is an axis system, including: sinoatrial node (SAN)—atrial—atrioventricular node (AVN)—Bundle of His—Bundle Branches (left and right). The Bundle of His is a collection of heart muscle cells specialized for electrical conduction that transmits the electrical impulses from the AVN to the point of the apex of the fascicular branches. Complex arrhythmias disease typically occurs in these different areas. However, ECG is only half of a sine wave.

The second system, referred to as a cardiac work system, is a pump system (one for each complete contraction and relaxation of the heart), which is done by the heart muscles. The main part of the second system is the left ventricle. In the traditional ECG, it is represented by the T wave or QT interval. There are about 10 million ventricular myocardial cells, without nerves or tracts.

Features or waves of each heartbeat waveform have been known for more than a century to correspond to electrical signals activating various parts of the heart. For example, the P wave is known to result from an electrical signal directed from the SAN to the AV node activating the atrium of the heart, to the Bundle of His to the left and right Bundle Branches, and the T wave is known to result from a recovery electrical signal (ventricular depolarization and repolarization) sent to the ventricles of the heart after they have contracted. As a result, physicians are able to diagnose specific heart problems by analyzing the shapes and time of these waves.

It is thought that an ECG heartbeat waveform includes much more information about the anatomy of the heart that is not being used (scanning and displaying). In particular, it is thought that at least some of the waves in an ECG heartbeat waveform include subwaveforms that provide more detailed information about parts of the heart, as described above. Consequently, there is a need for systems and methods for processing biological electrical signals, such as signals read by ECG, in order to provide additional information about anatomical structures.

Also, electrocardiogram information itself contains a lot of information that has not been discovered so far, leaving numerous puzzles in a clinical application.

In various embodiments, new waveforms are created from a conventional ECG waveform. New indexes and new parameters are obtained from the new waveforms, so that it is possible to have a breakthrough in electrocardiogram diagnostics.

In various embodiments, heart signals are divided into different frequency bands, and then convolved or combined in one diagram. For example, 16 different frequency bands can be used. This procedure is based on the study of ergonomics and analysis procedures for frequently used information in cybernetics and nonlinear theory. The procedure makes use of the theory and analysis index of an "electrocardiogram multi-phase signal," and by using a new method of frequency division and dimension division, according to the display method of P, Q, R, S, T, U, and J waveforms P-QRS-T in a conventional ECG waveform. Heart diseases are also related to and/or complicated by different other diseases. Therefore, different numbers of frequency ranges are required to be displayed as a diagnostic requirement, because the frequency shifts of various diseases are different. In the multi-domain frequency division method, 8, 9, 10, 11, 12, 13, 14, 15, or 16 roots of multi-domain linear waveforms are displayed, and a total of 12 leads are individually displayed. If each lead is divided into 16 waveforms, there are totally 192 ECG waveforms, providing much more information. In various embodiments, multi-domain ECG (mdECG) can be used as a very valuable and new diagnostic technique for combined heart diseases. This technique can be applied in electrocardiograph, monitor, echocardiography, and invasive electrophysiological instrument.

Since the invention of ECG, the linear waveform shaped like a rope has been used. Its frequency response range is 0-150 Hz and all subwaveforms are convolved or combined together. However, heart signals are formed by combining different ultra-low frequency, low frequency, intermediate frequency, high frequency, and ultra-high frequency signals. Because in ECG all frequencies are convolved together, many fine, weak, and very valuable signals are usually submerged or overlapped by the high frequency; especially at ventricle (ECG at T-wave, ECG 'T' wave duration) and atrium (ECG at P-wave, ECG 'P' wave duration), and numerous signals accumulate within a very small time axis range, causing problems and confusion in accuracy of ECG diagnosis rate. As a result, the detection rate of ECG for acute myocardial infarction (AMI), acute coronary syndrome (ACS), coronary artery disease (CAD), myocardial infarction (MI), heart failure (HF) etc., with the highest incidence of cardiovascular disease is only 17%-25%. Based on a large number of literature and research reports, for the CAD/MI/ACS patient, ECG begins to change only after ischemia reaches 70%, and only about half of the electrocardiograms show abnormality. There are 7 billion people in the world, and the percentage of people who die of cardiovascular diseases or complicated cardiovascular diseases is about 42.86% (3/7). Electrocardiogram is the most fundamental clinical assessment instrument, and it is simple, fast and economical. Therefore, it is important to improve the clinical ECG diagnosis rate, which is possible only by improving the waveform display rate of ECG.

In various embodiments, systems and methods improve the waveform display rate of ECG and clinical diagnosis rate using a 16 linear multi-domain electrocardiogram. Because the heart signals are separated according to different frequency bands with frequency bands being recombined, many high frequency signals, ultra-high frequency signal, low frequency signals, and ultra-low frequency signals are displayed with the raw heart signals at different frequency band according to the heart transduction pathway and electrophysiological rule, without the electrocardiogram being altered, i.e., at X-transverse axis and Y-vertical axis of P-QRS-T. Because the frequency bands of ECG are combined signals, mdECG separates the signals, i.e., separates them into independent waveforms consisting of different frequency bands. In this way, those frequency bands with the one linear waveform invisible and obscure in traditional ECG can be displayed clearly with different frequency bands one by one, assisting the doctor in reading, analyzing, judging and basic clinical assessment.

Figure 18:
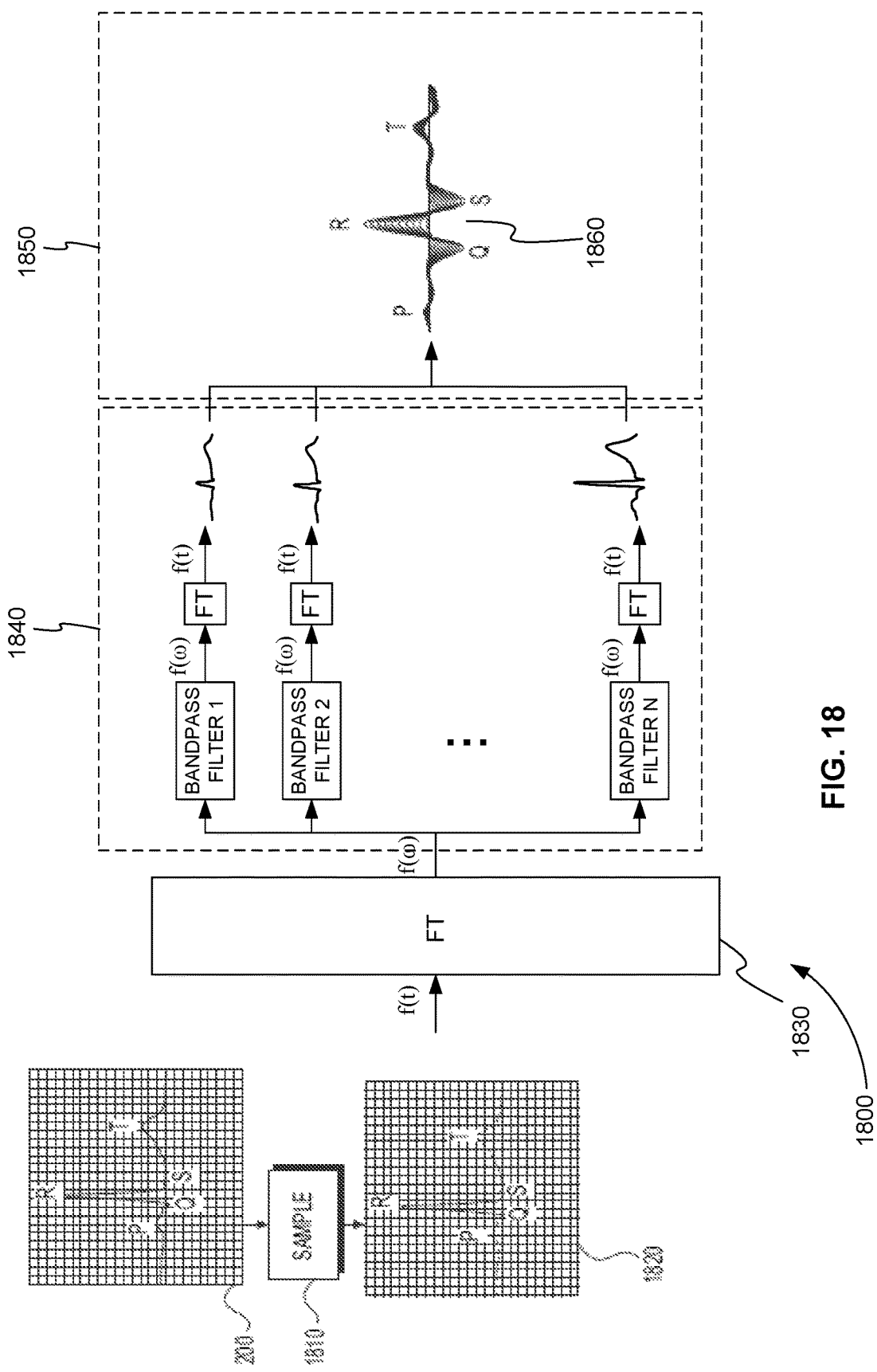
FIG. 18 is an exemplary block diagram showing a system for performing multi-domain ECG using 16 different frequency bands or domains, in accordance with various embodiments.

FIG. 18 is an exemplary block diagram 1800 showing a system for performing multi-domain ECG using 16 different frequency bands or domains, in accordance with various embodiments. Sampling block 1810 samples the electrical impulses at one electrode for one heartbeat, for example. This is shown graphically in FIG. 1800 by converting ECG waveform 200 to sampled ECG waveform 1820 using block 1810. The electrical impulses for the entire ECG waveform 200 are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 18, block 1830 converts sampled ECG waveform 1820 to a frequency domain signal. The time domain signal is converted into a frequency domain signal using a Fourier transform, for example.

As described above, through animal and/or human experimentation, the frequency bands associated with different muscles of the heart can be determined. The frequency bands used here can be based on those bands determined experimentally, for example. Alternatively, the 16 frequency bands can be found by dividing the total frequency bands 16 ways. The different band can have the same bandwidth or can have different bandwidths.

In block 1840, 16 different band pass filters filter sampled ECG waveform 1820's frequency domain signal into 16 different frequency domain signal. These 16 different 16 different frequency domain signals are then converted back to the time domain. The result of block 1840 is 16 different time domain signals.

In block 1850, the 16 different time domain signals are combined or plotted together in the time domain as one multi-domain ECG waveform 1860. In FIG. 1800, a conventional ECG signal from one electrode is processed into a multi-domain ECG waveform that includes 16 different time domain signals. In various embodiments, a conventional ECG signal from one electrode, however, can be processed into a multi-domain ECG waveform that includes any number of different time domain signals.

Figure 19:
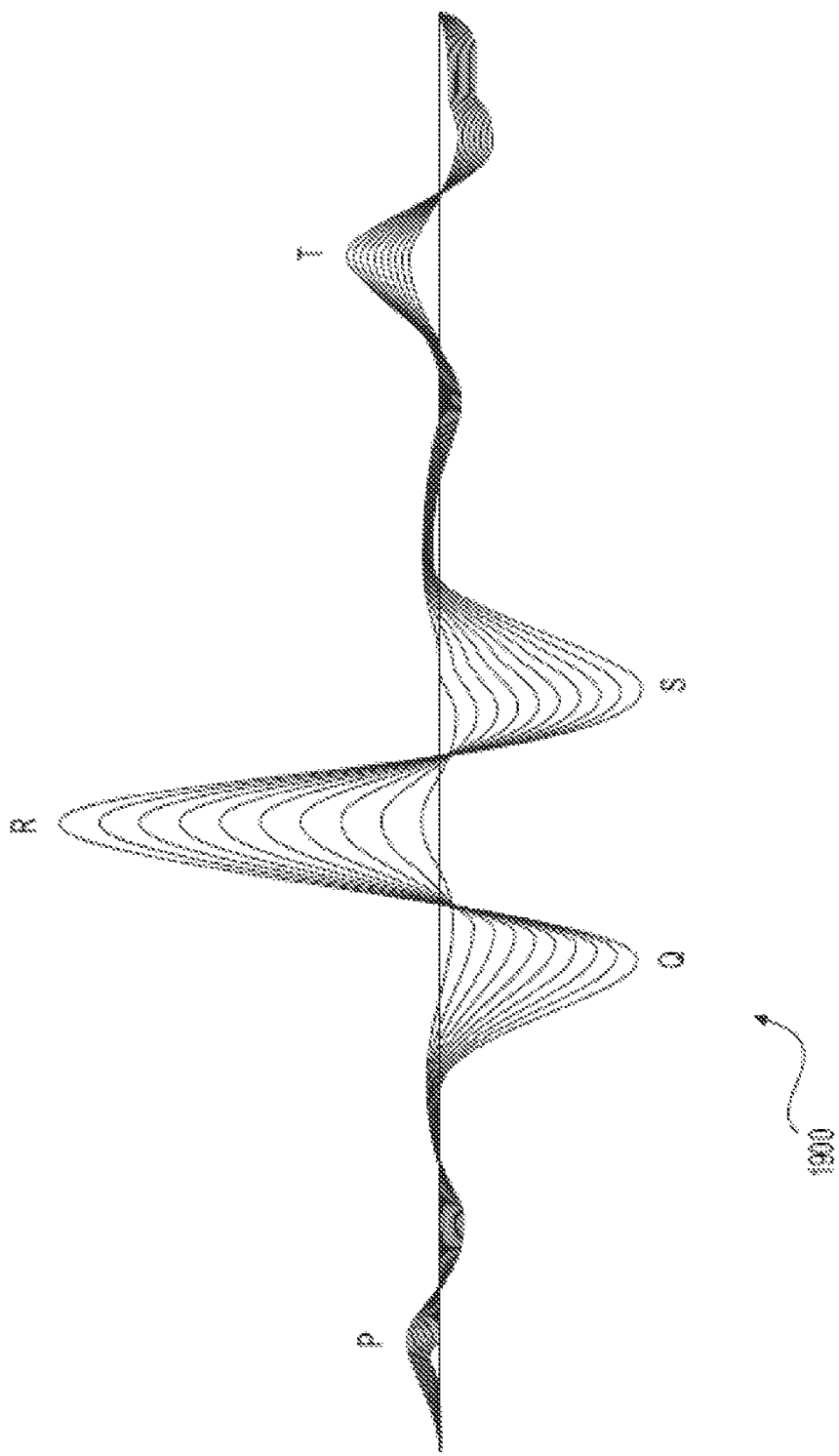
FIG. 19 is an exemplary plot of a multi-domain ECG waveform that includes 10 different time domain signals, in accordance with various embodiments.

FIG. 19 is an exemplary plot 1900 of a multi-domain ECG waveform that includes 10 different time domain signals, in accordance with various embodiments.

Figure 20:
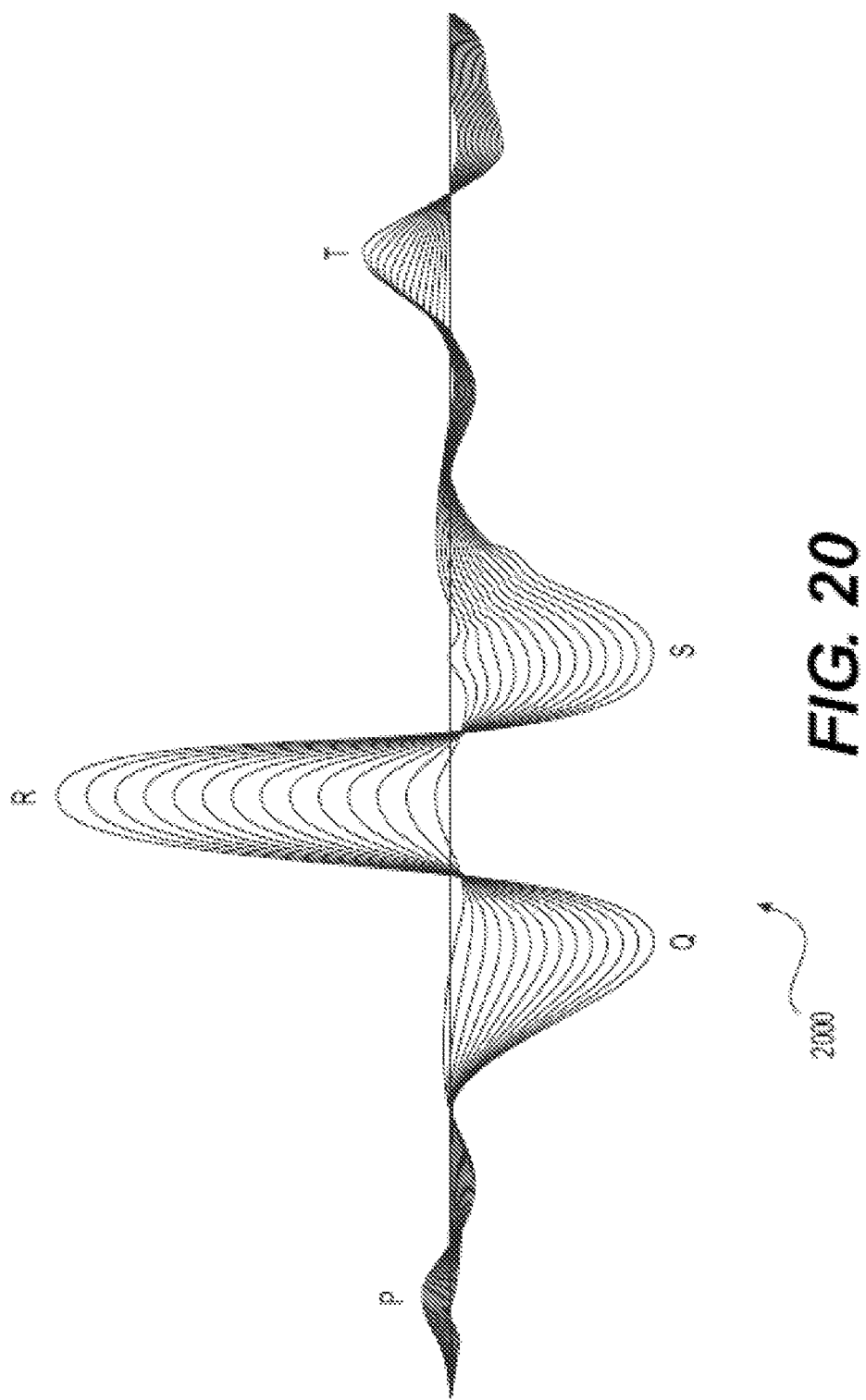
FIG. 20 is an exemplary plot of a multi-domain ECG waveform that includes 14 different time domain signals, in accordance with various embodiments.

FIG. 20 is an exemplary plot 2000 of a multi-domain ECG waveform that includes 14 different time domain signals, in accordance with various embodiments.

Figure 21:
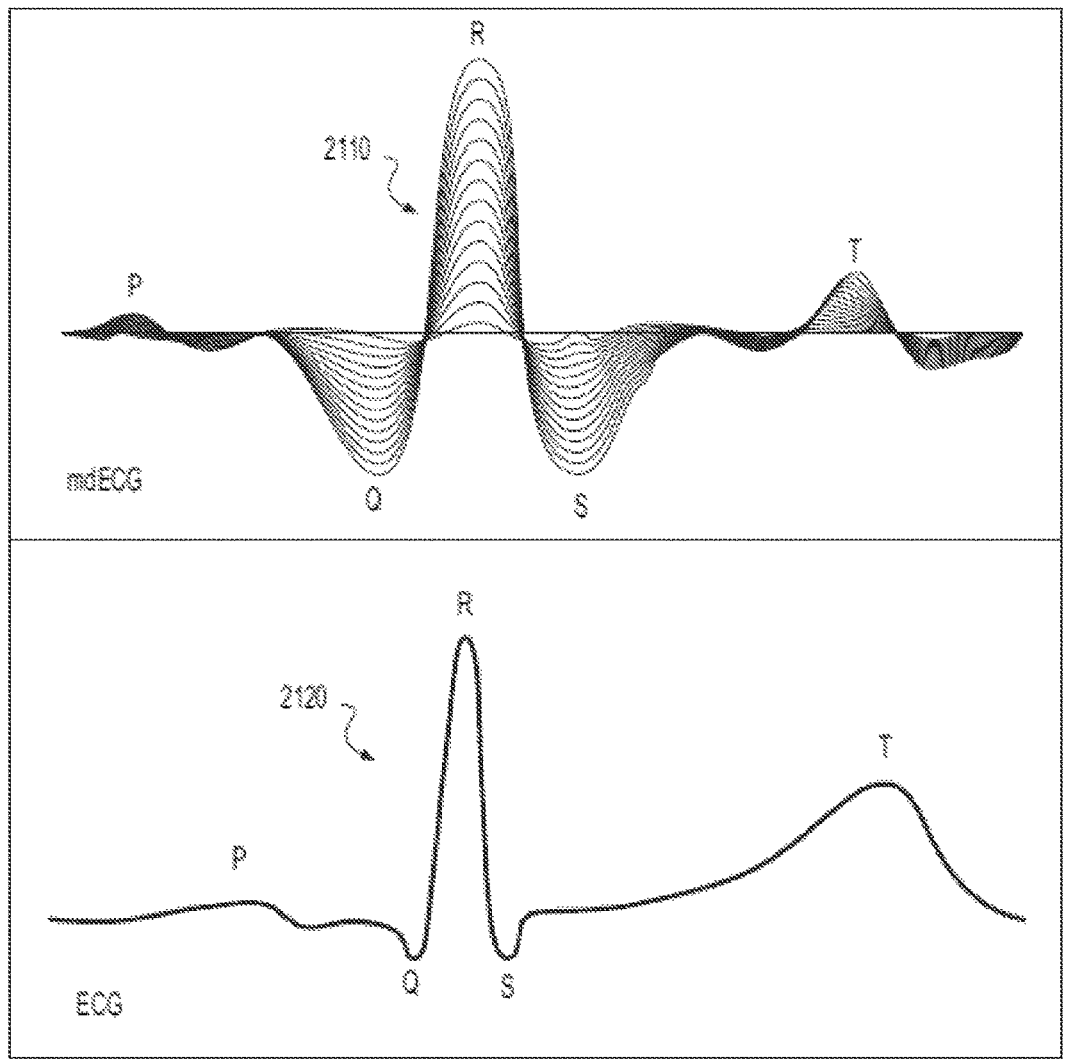
FIG. 21 is an exemplary alignment of a multi-domain ECG waveform 2110 that includes 16 different time domain signals with a conventional ECG waveform 2120, in accordance with various embodiments.

FIG. 21 is an exemplary alignment 2100 of a multi-domain ECG waveform 2110 that includes 16 different time domain signals with a conventional ECG waveform 2120, in accordance with various embodiments. Multi-domain ECG waveform 2110 is produced from conventional ECG waveform 2120 using the system depicted in FIG. 18, for example. As shown in FIG. 21, multi-domain ECG waveform 2110 can display data with negative values while conventional ECG waveform 2120 cannot.

In various embodiments, a multi-domain ECG waveform is generated for each electrode.

Figure 22:
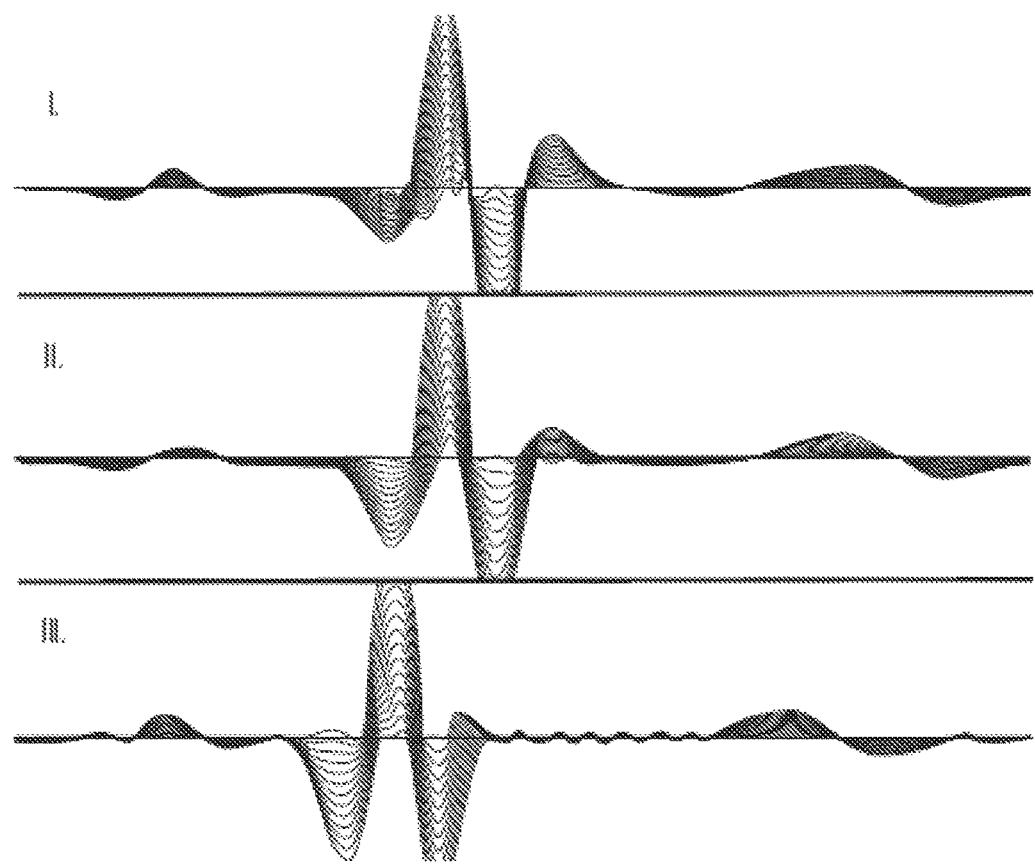
FIG. 22 is an exemplary diagram showing portions of the three multi-domain ECG waveform produced for three different ECG electrodes, I, II, and III, in accordance with various embodiments.

FIG. 22 is an exemplary diagram 2200 showing portions of the three multi-domain ECG waveform produced for three different ECG electrodes, I, II, and III, in accordance with various embodiments.

Converting a conventional ECG waveform into a multi-domain ECG waveform that includes many different time domain signals can provide important clinical information.

Figure 23:
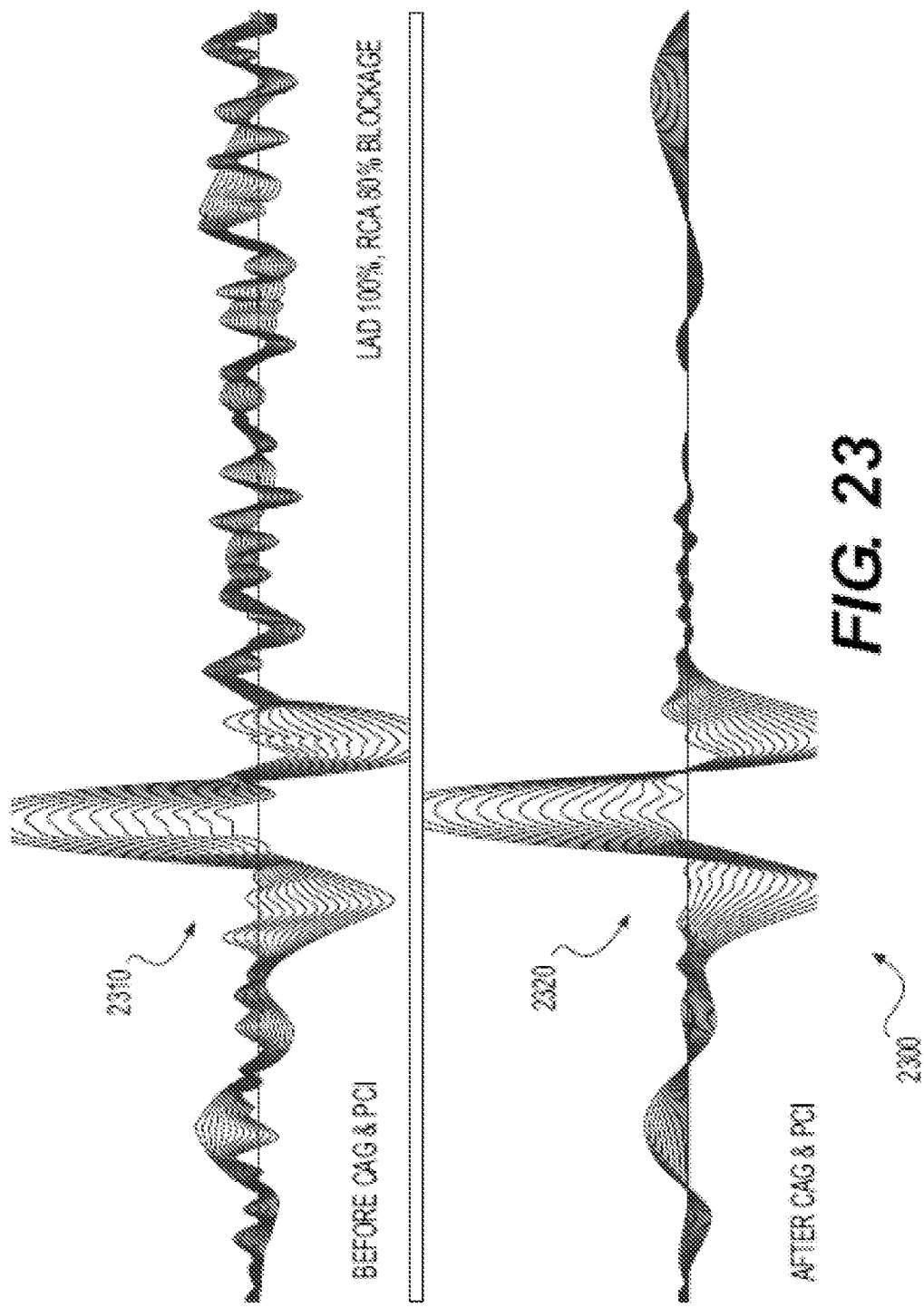
FIG. 23 is an exemplary alignment of multi-domain ECG waveforms measured for a patient with a 100% left anterior descending (LAD) artery and 80% right coronary artery (RAC) blockage before and after percutaneous coronary intervention (PCI, formerly known as angioplasty with stent), in accordance with various embodiments.

FIG. 23 is an exemplary alignment of multi-domain ECG waveforms measured for a patient with a 100% left anterior descending (LAD) artery and 80% right coronary artery (RAC) blockage before and after percutaneous coronary intervention (PCI, formerly known as angioplasty with stent), in accordance with various embodiments. Multi-domain ECG waveform 2310 was measured before PCI intervention. Multi-domain ECG waveform 2320 was measured after PCI intervention. Both waveforms are measured from the same electrode or lead (I). The differences in multi-domain ECG waveforms 2310 and 2320 shows the clinical value of such waveforms. In other words, multi-domain ECG waveforms can be used to diagnose specific conditions.

System for Detecting a Multi-Domain ECG Waveform

In various embodiments, an electrocardiography (ECG) system is provided for detecting a multi-domain ECG waveform that includes two or more different time domain signals that each represent a different frequency domain signal. Returning to FIG. 8, the ECG system includes two or more electrodes 810, a detector 820, a signal processor 830, and a display device 840.

Two or more electrodes 810 are placed proximate to a beating heart and receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on the surface of the heart or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses. In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor 830 receives the ECG waveform from detector 820. Signal processor 830 converts the ECG waveform to a frequency domain waveform. Signal processor 830 separates the frequency domain waveform into two or more different frequency domain waveforms using two or more different bandpass filters. Finally, signal processor 830 converts the two or more different frequency domain waveforms into two or more different time domain waveforms.

Signal processor 830 separates the frequency domain waveform into two or more different frequency domain waveforms by dividing the frequency band of the ECG waveform into two or more different frequency bands and filtering the two or more different frequency bands using the two or more different bandpass filters, for example. In various embodiments, each of the two or more different frequency bands has the same bandwidth. In various alternative embodiments, each of the two or more different frequency bands can have different bandwidths. In various embodiments, the two or more different frequency bands are contiguous across the frequency band of the ECG waveform. In various alternative embodiments, the two or more different frequency bands are not contiguous across the frequency band of the ECG waveform.

Signal processor 830 can be a separate device, can be software running on device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general purpose processor. A general purpose processor can include, but is not limited to, a microprocessor, a micro controller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820.

Display device 840 displays the two or more different time domain waveforms in the same time domain plot as the ECG waveform for the at least one heartbeat of the beating heart. As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record multi-domain ECG waveforms, multi-domain ECG data and conventional ECG waveforms and data. The memory device can be, but is not limited to, a volatile electronic memory, such as random access memory (RAM), a non-volatile electronic memory, such as electrically erasable programmable read-only memory (EEPROM or Flash memory), or a magnetic hard drive.

In various embodiments, display device 840 further displays the ECG waveform for at least one heartbeat of the beating heart. Display device 840 further aligns the display of the multi-domain ECG waveform and the display of ECG waveform in the time domain.

In various embodiments, display device 840 displays each time domain waveform of the two or more different time domain waveforms in a different color. In various alternative embodiments, display device 840 displays each time domain waveform of the two or more different time domain waveforms in a different pattern of dashes.

Method for Detecting a Multi-Domain ECG Waveform

Figure 24:
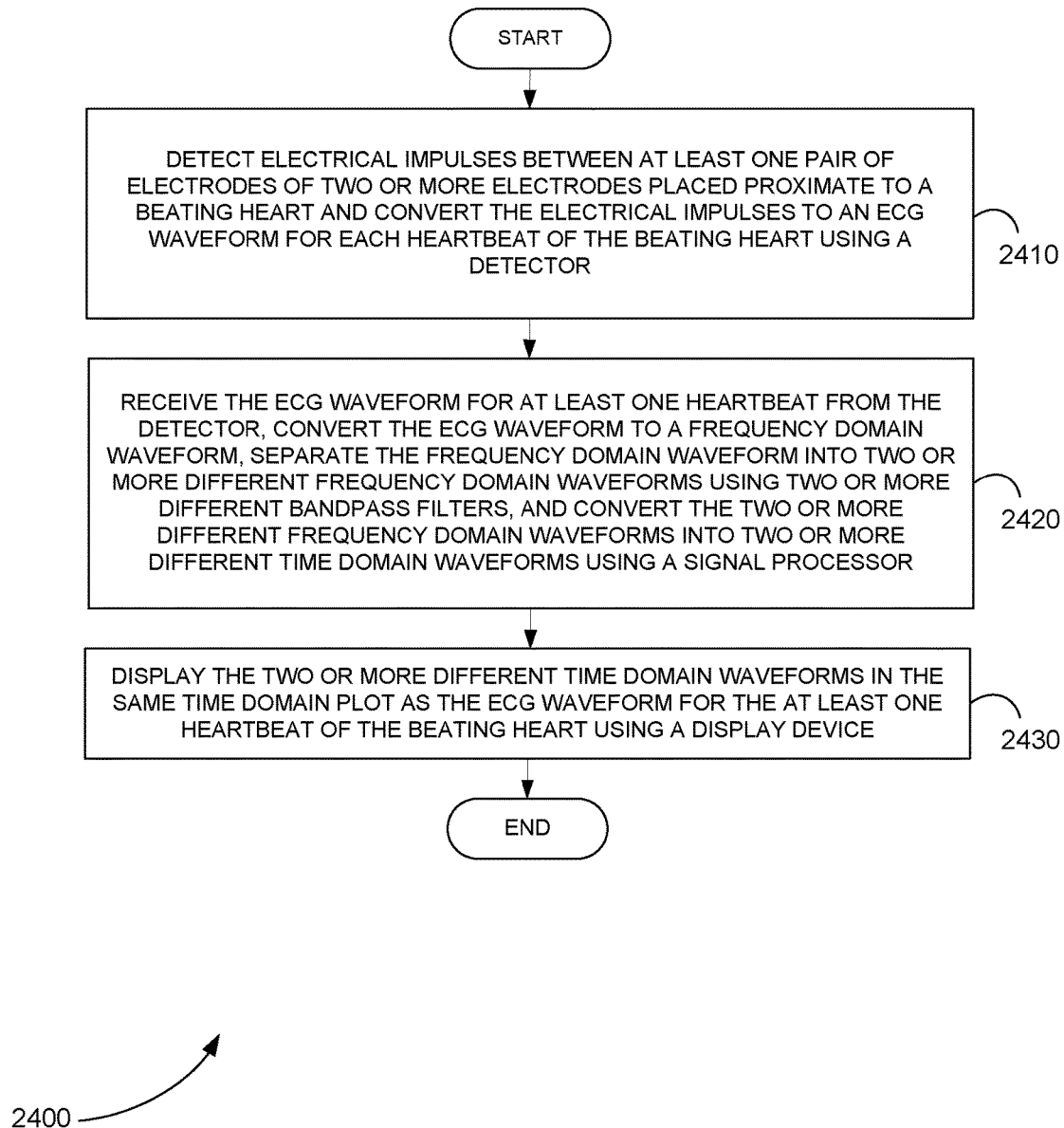
FIG. 24 is a flowchart showing a method 2400 for detecting a multi-domain ECG waveform that includes two or more different time domain signals that each represent a different frequency domain signal, in accordance with various embodiments.

FIG. 24 is a flowchart showing a method 2400 for detecting a multi-domain ECG waveform that includes two or more different time domain signals that each represent a different frequency domain signal, in accordance with various embodiments.

In step 2410 of method 2400, electrical impulses are detected between at least one pair of electrodes of two or more electrodes placed proximate to a beating heart using a detector. The electrical impulses are converted to an ECG waveform for each heartbeat of the beating heart using the detector.

In step 2420, the ECG waveform for at least one heartbeat is received from the detector, the ECG waveform is converted to a frequency domain waveform, the frequency domain waveform is separated into two or more different frequency domain waveforms using two or more different bandpass filters, and the two or more different frequency domain waveforms are converted into two or more different time domain waveforms using a signal processor.

In step 2430, the two or more different time domain waveforms are displayed in the same time domain plot as the ECG waveform for the at least one heartbeat of the beating heart using a display device.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Cardiac Electrophysiological Markers

The right and left ventricles consist of the myocardial cells, as described above. Currently, there are no invasive or noninvasive methods of checking or measuring the electrical activity of these cells, other than the half sine T wave of traditional or conventional ECG. These cells play an important role in the most prevalent cardiovascular diseases, such as acute myocardial infarction (AMI), acute coronary syndrome (ACS), coronary artery disease (CAD), myocardial infarction (MI), heart failure (HF), etc. However, the detection rate of traditional ECG for these diseases is only 17%-25%.

In various embodiments, new cardiac and myocardium markers are added to the display of a multi-domain ECG waveform. These markers are shown along the x-axis and adjacent to small signals or subwaveforms that are obvious to the naked eye. From these markers and subwaveforms, new parameters are measured.

Based on the study of ergonomics and analysis procedures for some frequently used information in cybernetics and nonlinear theory, the multi-domain ECG waveform described above was developed. In multi-domain ECG the conventional ECG heart signals are divided into 16 or 32 different frequency bands and then displayed together. Heart diseases are also related to and/or complicated by different other diseases. Therefore, different numbers of frequency ranges are required to be displayed as a diagnostic requirement, because the frequency shifts of various diseases are different. In the multi-domain frequency division method, 8, 9, 10, 11, 12, 13, 14, 15, 16, 17, 18, 19, 20, 21, 22, 23, 24, 25, 26, 27, 28, 29, 30, 31 or 32 roots of multi-domain linear waveforms are displayed, and a total of 12 leads can be individually displayed. If each lead is divided into 32 waveforms, then there are totally 384 multi-domain ECG waveforms, providing more information. Multi-domain ECG waveforms make it possible to develop new cardiac markers for combined heart diseases. The new multi-domain ECG waveforms with cardiac markers can be applied in Electrocardiograph, Holter, Monitor, Echocardiography, and Invasive Electrophysiological instruments.

As described above, multi-domain ECG waveforms can provide a full information multi-band and multi-linear electrophysiological cardiogram. Since the multi-domain ECG technique is able to record various multi-band, multi-track linear electric signals of cardiac electrophysiological activities that correspond to different regions of the entire heart, the multi-domain ECG technique is hereinafter referred to as an "electrophysiocardiogram" (EPCG).

Regardless of whether it has been obtained through an invasive or non-invasive approach, a traditional ECG is always represented by a single characteristic wave form, which resembles a string. Accordingly, it may bury certain comprehensive, various or mixed cellular action potential signals, and certain electric signals of various anatomic locations. For a long period of time, traditional ECG has had a lot of mysteries surrounding it, because of these convolved signals buried within it.

Traditional ECG, therefore, limits the amount of the signals that are discernable and determinable. It is well known that heart is a flexible organ, and that it is located in a closed electromagnetic field. In this regard, an overall cardiac electric signal may be formed by a wide variety of different automatic conduction system potentials, different cellular action potentials, as well as the electric signals originated from atrial myocardium and ventricular myocardium. From the EPCG waveform, it can be seen that 95% of the multi-band signals are originated from atrial myocardium and ventricular myocardium, which indicates that the electrocardiac signal is actually not a single sinusoidal wave. For the first time, EPCG technology allows cardiac signals to be gathered into a linear wave form, which is then processed through various new approaches featuring multiple frequency bands, multiple dimensions and multiple patterns, and recorded as the following types of signals within the ranges of P wave and T wave: multiple frequency band signals, signals of different regions and different locations, forward waves and negative waves. In addition, EPCG can also record certain small signals (subwaveforms) that are located above or below the x-axis (close to the x-axis), as well as the small signals that exhibit certain specific local characteristics, such as time, amplitude, phase, overlapping, crossing and other spatial features.

In addition, the EPCG signals are synchronous with the traditional ECG signals and correspond completely to the P-QRS-T shown in a traditional ECG. Therefore, EPCG can help to solve many puzzling scientific questions regarding the heart, such as exactly how many electric signals are involved in heart excitation, pacing, conduction, and action, as well as many other intriguing questions about heart. In this way, it is able to make the field of ECG and related electrophysiological disciplines easier and more straightforward, and thus more useful in clinical practice.

In various embodiments, EPCG can increase the use of ECG in clinical diagnosis. In EPCG, the heart signals are separated according to different frequency bands and are then displayed together. Many high frequency signals, ultra high frequency signals, low frequency signals, and ultra-low frequency signals are displayed. These heart signals at different frequency bands are shown in conjunction with the heart transduction pathway and electrophysiological rules and without the electrocardiogram being altered, i.e., at the x-transverse axis and the y-vertical axis of P-QRS-T. In contrast to traditional ECG, where the frequency bands are combined or convolved, EPCG separates the signals, i.e., separates them into independent waveforms consisting of different frequency bands. Cardiac electrophysiological markers shown with the different frequency bands can further assist the doctor in reading, analyzing, and making a basic clinical assessment.

The nervous and self-conduction system of the heart is composed of sympathetic nerve and parasympathetic nerveanatomical regions: SAN to Atrial to AVN to Bundle of His to left and right Bundle Branches to Purkinje's fibers. These regions have different frequencies and frequency bands, constructed individually and displayed together in EPCG. Thus, the heart signals are separated and the frequencies are separated, and it is possible to display more signals.

Figure 25:
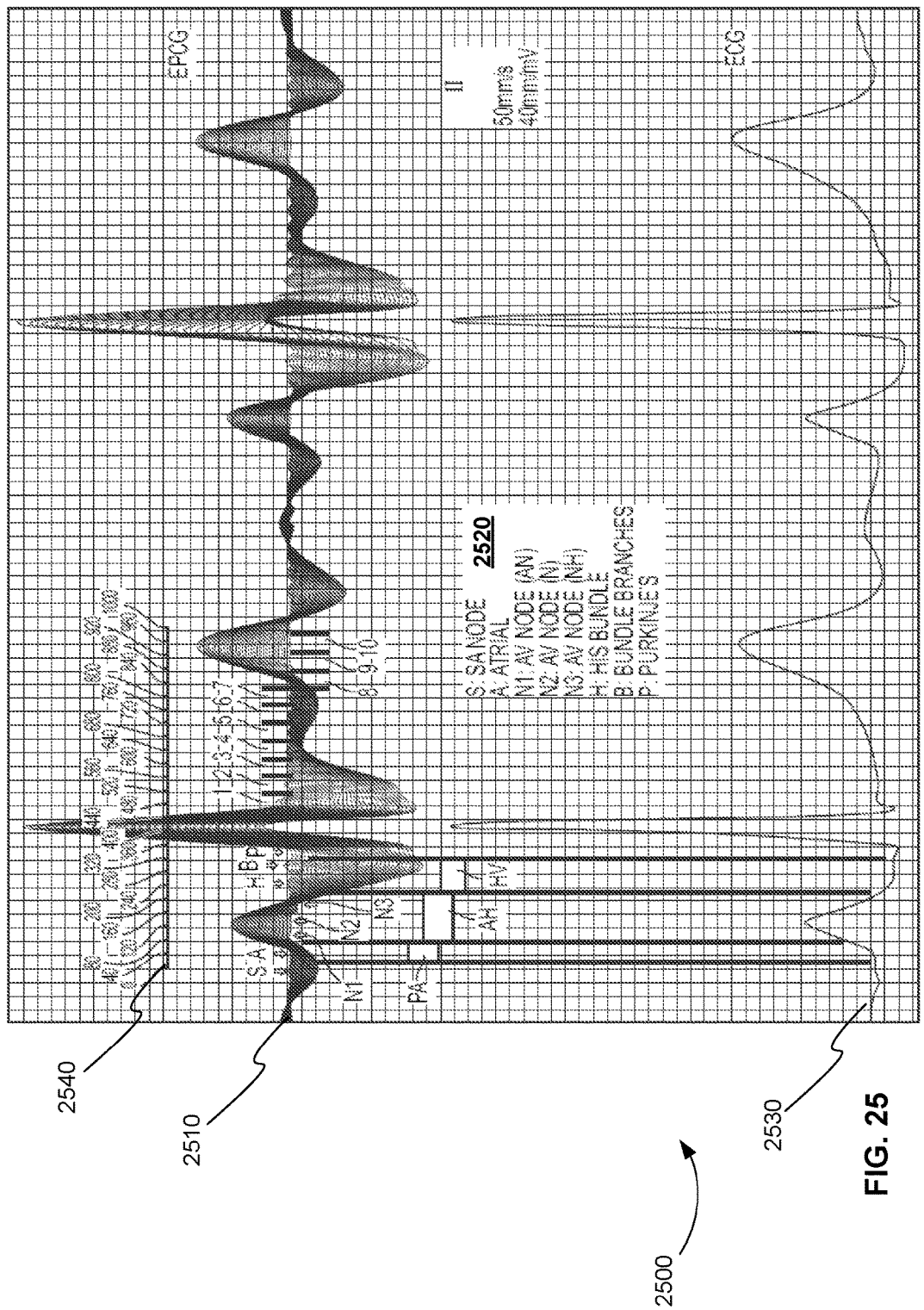
FIG. 25 is an exemplary time domain plot from an electrophysiocardiogram (EPCG) showing a multi-domain ECG waveform that includes 32 multi frequency waveforms and showing cardiac electrophysiological markers to aid in clinical diagnosis, in accordance with various embodiments.

FIG. 25 is an exemplary time domain plot 2500 from an EPCG showing a multi-domain ECG waveform that includes 32 multi frequency waveforms and showing cardiac electrophysiological markers to aid in clinical diagnosis, in accordance with various embodiments. Two heartbeats of multi-domain ECG waveform 2510 are shown. Cardiac electrophysiological markers are displayed for the first heartbeat.

Two types of cardiac electrophysiological markers are displayed: heart cell markers and electrophysiological interval markers. The heart cell markers are also of two types: cardiac self-conduction markers and myocardium markers. The cardiac self-conduction markers are shown in table 2520. These markers include S:SANODE, A:ATRIAL, N1:AV NODE (AN), N2:AV NODE (N), N3:AV NODE (NH), H: HIS BUNDLE, B:BUNDLE BRANCHES, and P:PURKINJE'S. Each cardiac self-conduction marker in FIG. 25 is shown along the x-axis of multi-domain ECG waveform 2510 with an arrow pointing to the location or expected location of the subwaveform representing the type of heart cells or fibers. Cardiac self-conduction markers can point to the expected time location of a subwaveform of a normal heart, or cardiac self-conduction markers can point to the current location of a subwaveform inferred from the waveforms being measured, such as multi-domain ECG waveform 2510.

The myocardium markers are shown in FIG. 25 as a number of delimited regions along the x-axis. These regions are numbered from 1 to 10 in FIG. 25. Each region delimited by myocardium markers includes the location or expected location of subwaveform representing myocardium cells. Myocardium markers appear in the ST-T region of the traditional ECG signal. Myocardium markers also can mark the expected regions of a normal heart, or myocardium markers can mark the current regions inferred from the waveforms being measured, such as multi-domain ECG waveform 2510.

The electrophysiological interval markers are also shown in FIG. 25 as a number of delimited regions along the x-axis. These electrophysiological interval markers include PA, AH, and HV. The PA interval is the interval from the onset of the P wave to the onset of an atrial intracardiac signal, for example. The AH interval shows the conduction time through the AV node, for example. The HV interval displays the conduction time from the His bundle to the first ventricular activation. Electrophysiological interval markers also can mark the expected regions of a normal heart, or electrophysiological interval markers can mark the current regions inferred from the waveforms being measured, such as multi-domain ECG waveform 2510.

The electrophysiological interval markers in FIG. 25 extend from multi-domain ECG waveform 2510 to traditional ECG waveform 2530. As a result, the differences between multi-domain ECG waveform 2510 and traditional ECG waveform 2530 in these electrophysiological intervals can easily be seen.

A time scale 2540 is shown above the cardiac electrophysiological markers in FIG. 25. This time scale allows the timing of the subwaveforms of multi-domain ECG waveform 2510 to be determined with respect to any of the cardiac electrophysiological markers.

Note that multi-domain ECG waveform 2510 can display data with negative values, while traditional ECG waveform 2530 cannot.

Figure 26:
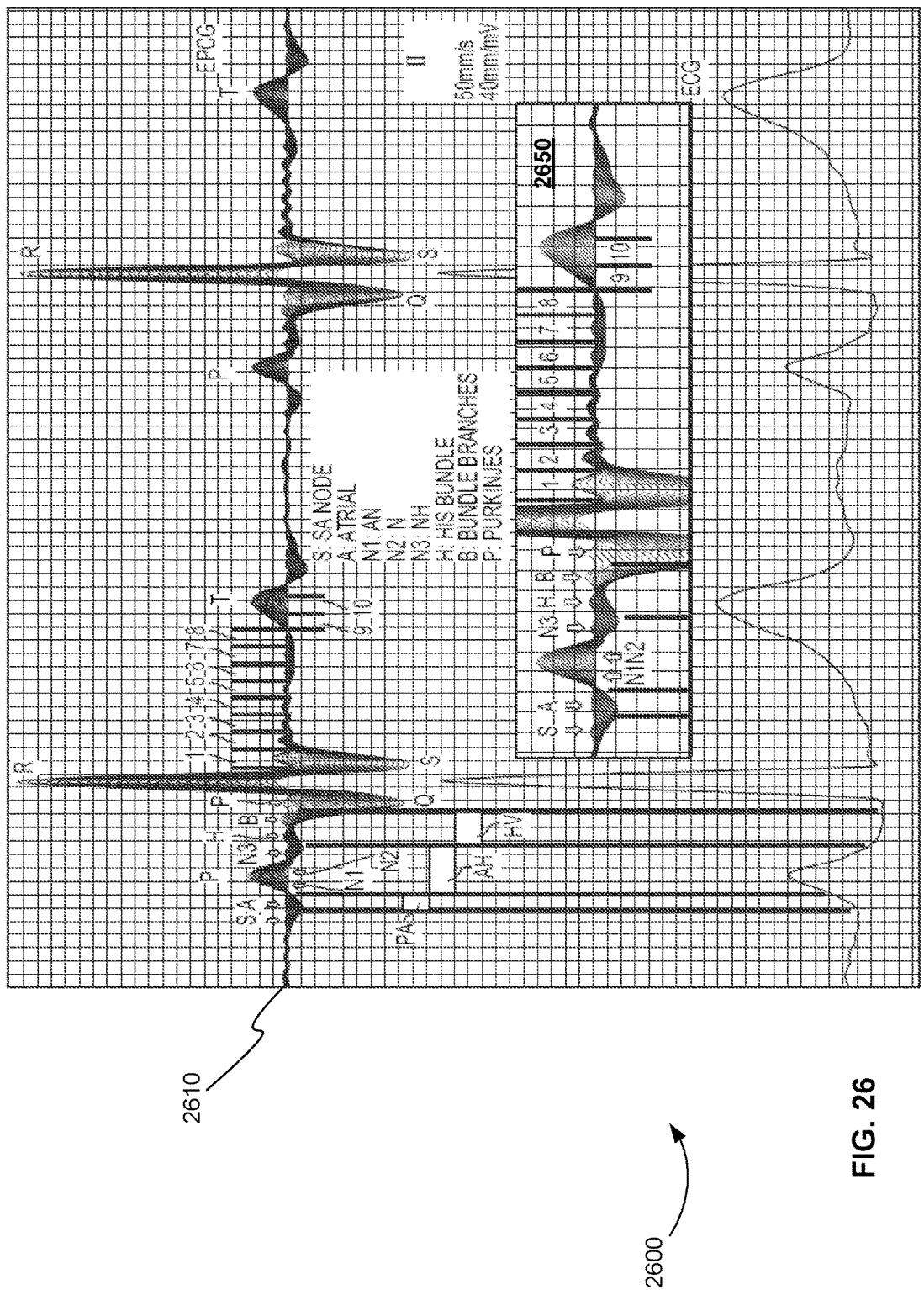
FIG. 26 is an exemplary time domain plot from an EPCG showing a multi-domain ECG waveform that includes fewer than 32 multi frequency waveforms and showing cardiac electrophysiological markers to aid in clinical diagnosis, in accordance with various embodiments.

FIG. 26 is an exemplary time domain plot 2600 from an EPCG showing a multi-domain ECG waveform that includes fewer than 32 multi frequency waveforms and showing cardiac electrophysiological markers to aid in clinical diagnosis, in accordance with various embodiments. Two heartbeats of multi-domain ECG waveform 2610 are shown. The same cardiac electrophysiological markers shown in FIG. 25 are displayed for the first heartbeat of FIG. 26. FIGS. 25 and 26 show that a multi-domain ECG waveform can be made up of time domain signals from different numbers of frequency bands. In addition, FIG. 26 provides window 2650 showing a zoomed in view of the heart cell markers.

Figure 27:
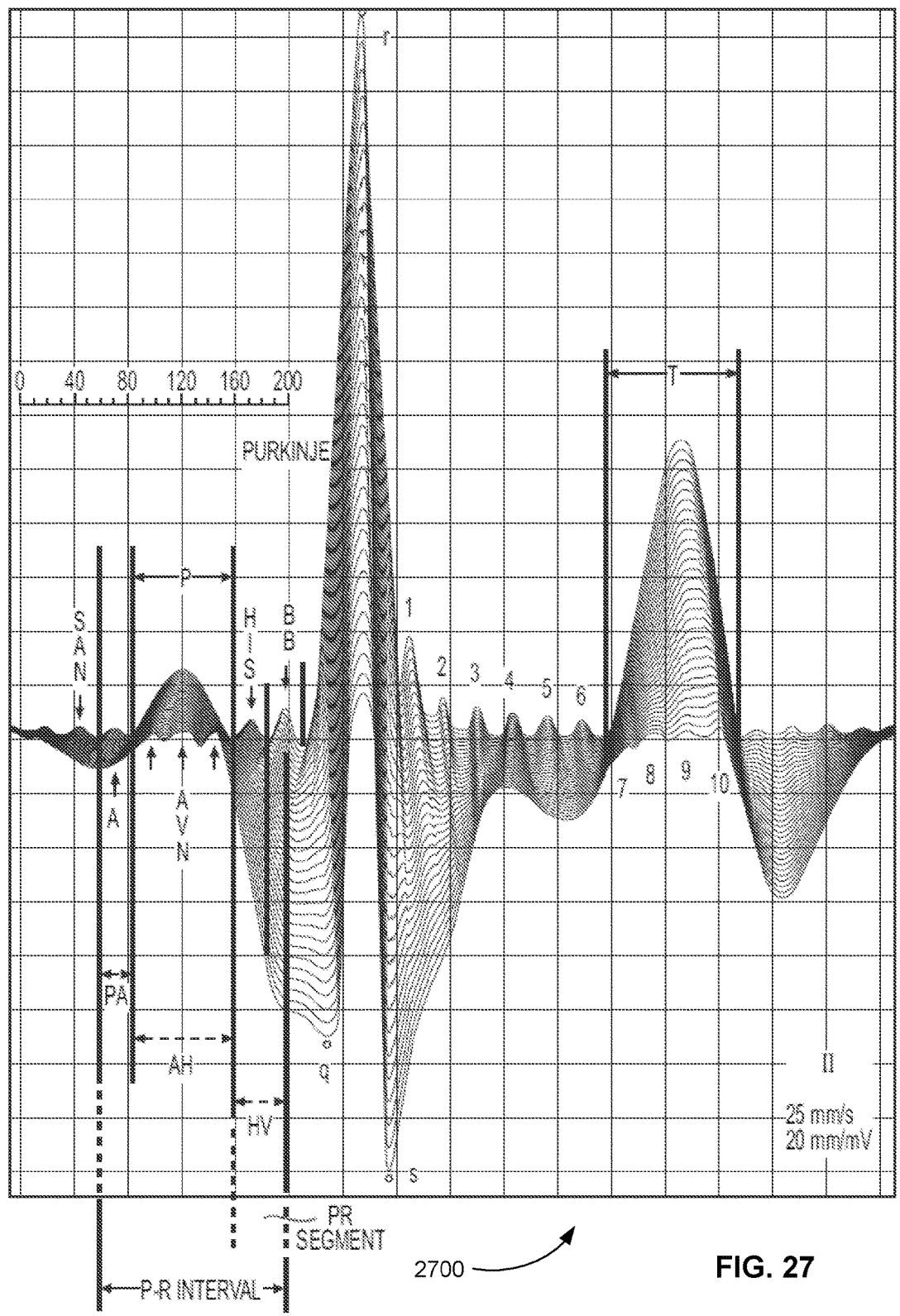
FIG. 27 is an exemplary time domain plot from an EPCG showing a multi-domain ECG waveform and showing cardiac electrophysiological markers for a single beat of a normal heart, in accordance with various embodiments.

FIG. 27 is an exemplary time domain plot 2700 from an EPCG showing a multi-domain ECG waveform and showing cardiac electrophysiological markers for a single beat of a normal heart, in accordance with various embodiments. FIG. 27 shows the normal EPCG electrocardiography signal for a II lead.

Figure 28:
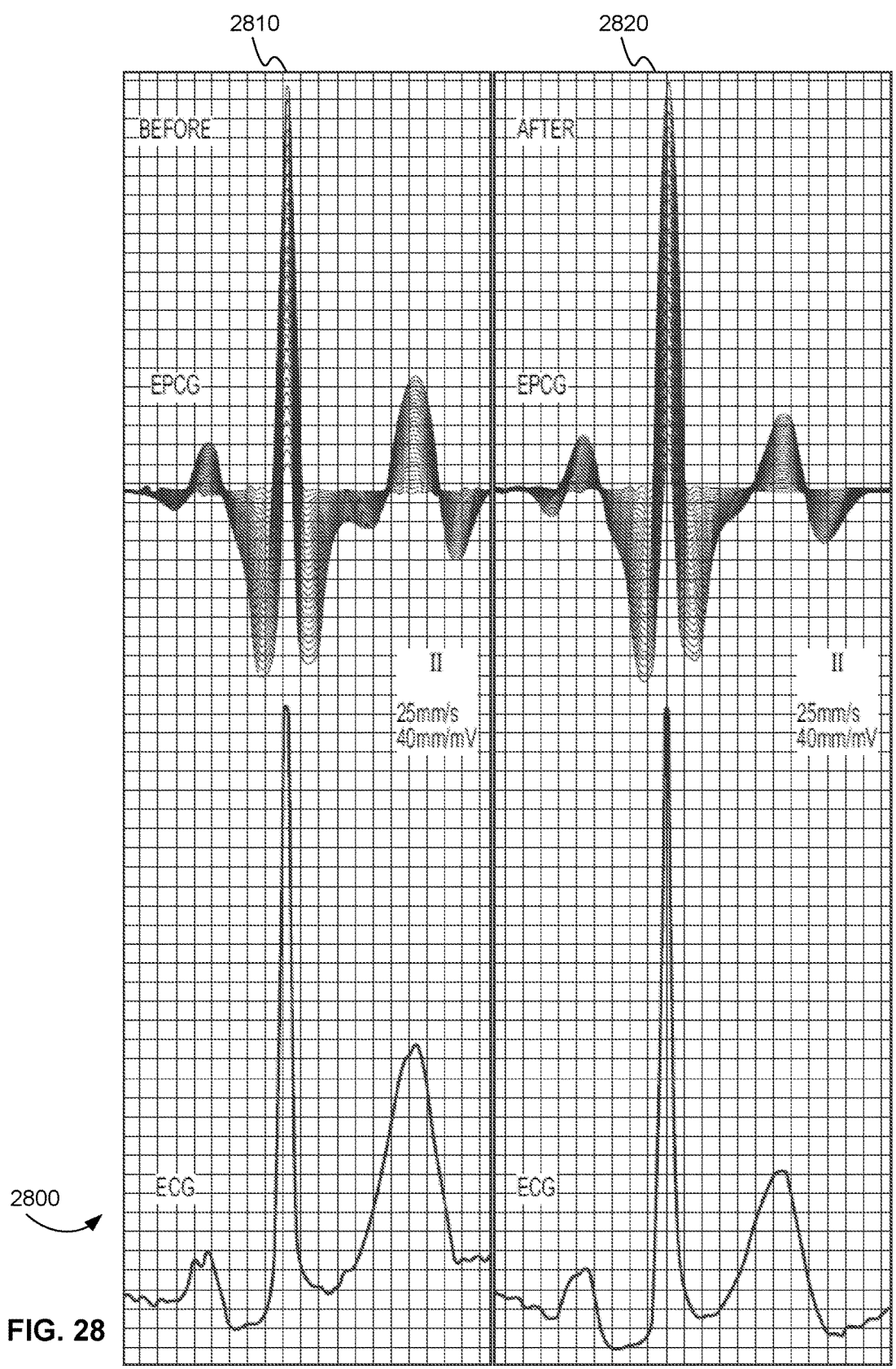
FIG. 28 is an exemplary comparison performed without cardiac electrophysiological markers of a time domain plot showing a multi-domain ECG waveform for a patient with coronary artery disease (CAD) before corrective surgery and a time domain plot showing a multi-domain ECG waveform for a patient with CAD after corrective surgery, in accordance with various embodiments.

FIG. 28 is an exemplary comparison 2800 performed without cardiac electrophysiological markers of a time domain plot 2810 showing a multi-domain ECG waveform for a patient with coronary artery disease (CAD) before corrective surgery and a time domain plot 2820 showing a multi-domain ECG waveform for a patient with CAD after corrective surgery, in accordance with various embodiments. FIG. 28 shows that it is difficult to see differences between plot 2810 and plot 2820 without cardiac electrophysiological markers.

Figure 29:
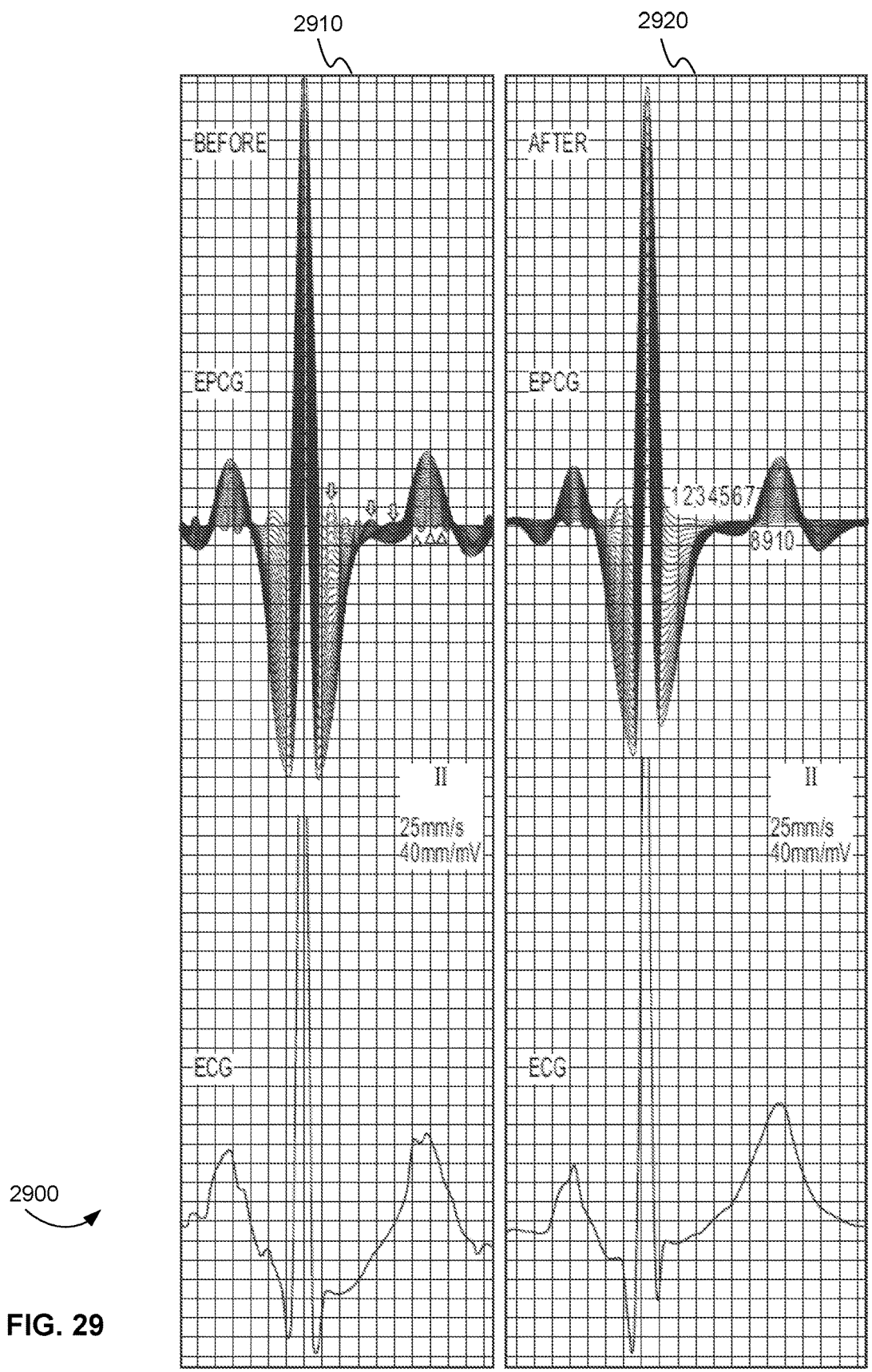
FIG. 29 is an exemplary comparison performed with cardiac electrophysiological markers of a time domain plot showing a multi-domain ECG waveform for a patient with CAD before corrective surgery and a time domain plot showing a multi-domain ECG waveform for a patient with CAD after corrective surgery, in accordance with various embodiments.

FIG. 29 is an exemplary comparison 2900 performed with cardiac electrophysiological markers of a time domain plot 2910 showing a multi-domain ECG waveform for a patient with CAD before corrective surgery and a time domain plot 2920 showing a multi-domain ECG waveform for a patient with CAD after corrective surgery, in accordance with various embodiments. FIG. 29 shows that it is much easier to see differences between plot 2910 and plot 2920 with cardiac electrophysiological markers.

Figure 30:
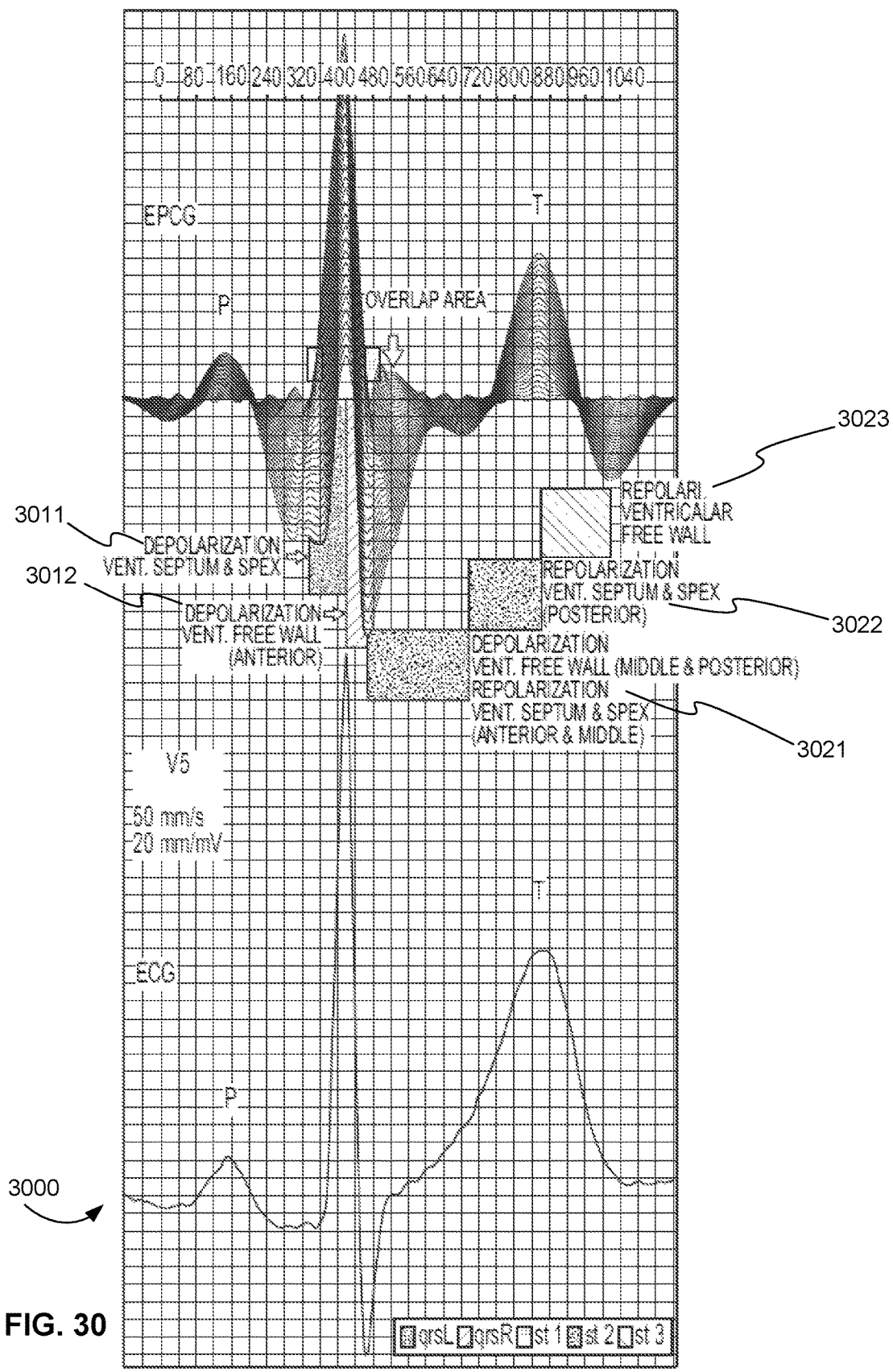
FIG. 30 is an exemplary time domain plot from an EPCG showing how a multi-domain ECG waveform can provide more information about ventricular depolarization and repolarization than traditional ECG, in accordance with various embodiments.

FIG. 30 is an exemplary time domain plot 3000 from an EPCG showing how a multi-domain ECG waveform can provide more information about ventricular depolarization and repolarization than traditional ECG, in accordance with various embodiments. In traditional ECG, the entire QRS interval is interpreted as depolarization and the entire ST-T interval is interpreted as repolarization. FIG. 27 shows that EPCG allows the QRS interval to be divided into two anatomical parts of the depolarization and the ST-T interval to be divided into three anatomical sites or parts. This shows that more minute electrophysiological signals are transmitted through the different anatomic sites of the heart.

For example, FIG. 30 shows that the QRS interval actually includes a depolarization ventricular septum and spex portion 3011 and a depolarization ventricular free wall (anterior) portion 3012. Similarly, FIG. 30 shows that the ST-T interval actually includes a depolarization ventricular free wall (middle and posterior) repolarization ventricular septum and spex portion 3021, a repolarization ventricular septum and spex portion (posterior) 3022, and a repolarization ventricular free wall portion 3023.

Figure 31:
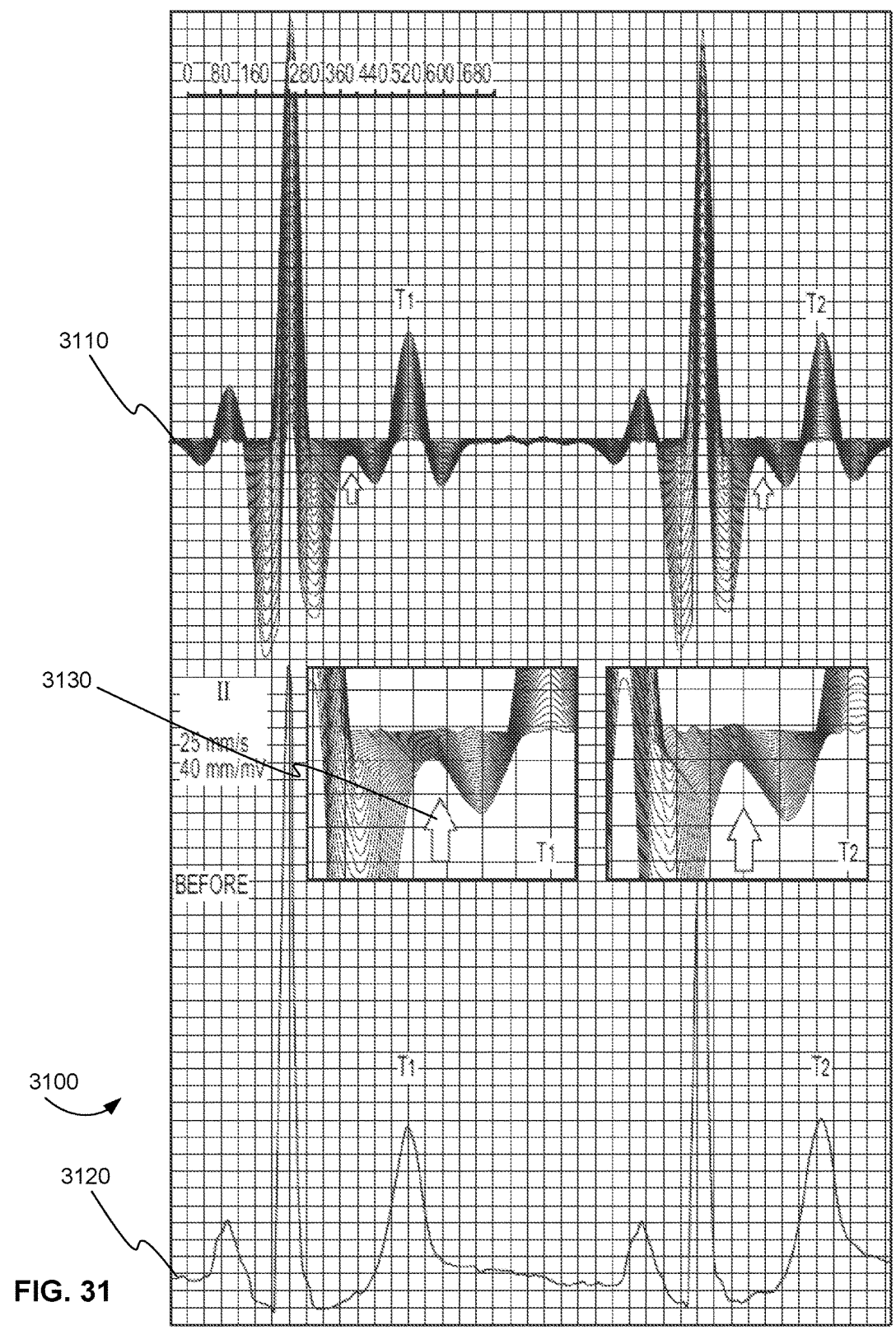
FIG. 31 is an exemplary time domain plot of an EPCG multi-domain ECG waveform for a CAD patient before percutaneous coronary angioplas (PTCA), in accordance with various embodiments.

FIG. 31 is an exemplary time domain plot 3100 of an EPCG multi-domain ECG waveform for a CAD patient before percutaneous coronary angioplasty (PTCA), in accordance with various embodiments.

Figure 32:
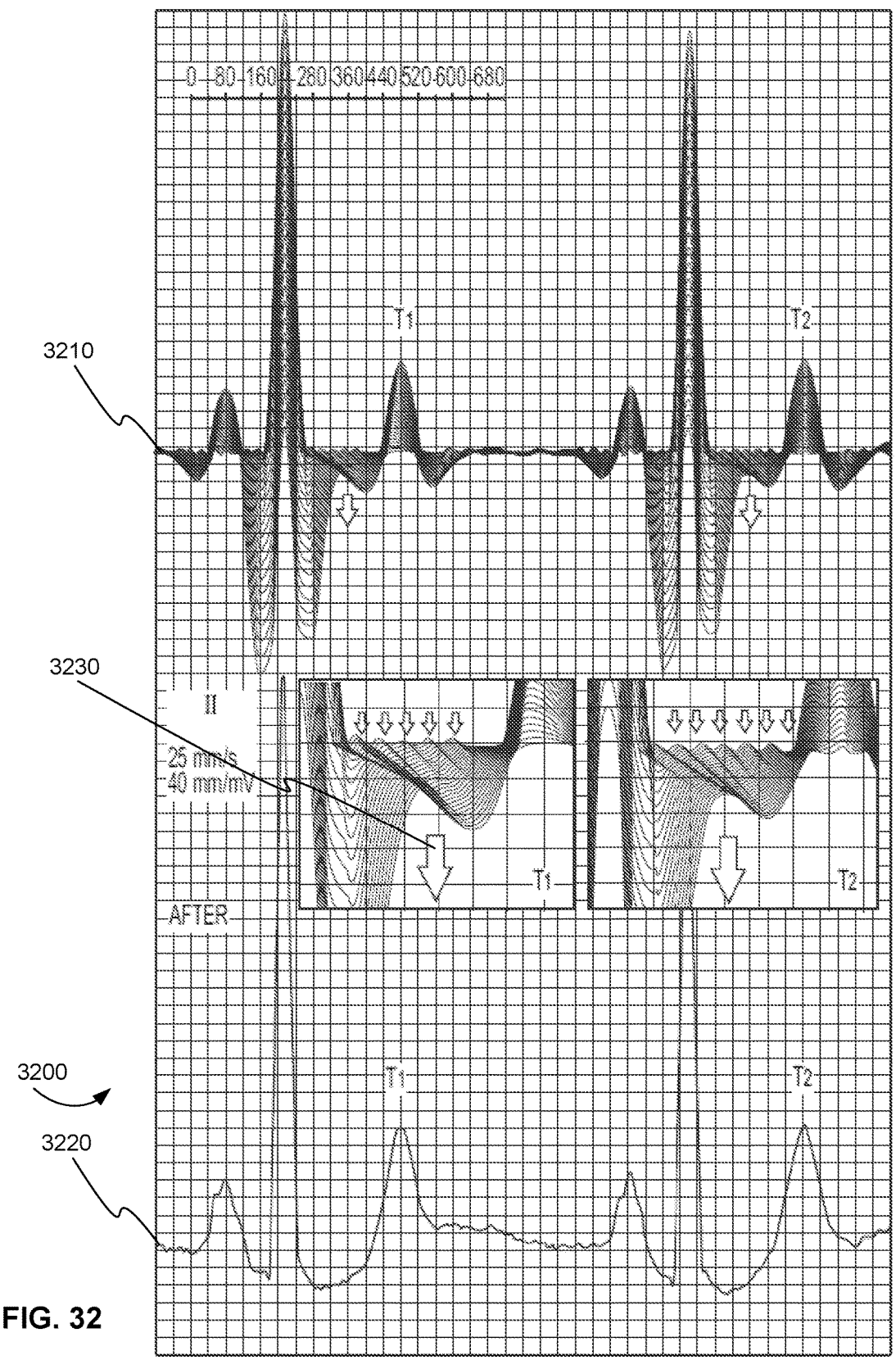
FIG. 32 is an exemplary time domain plot of an EPCG multi-domain ECG waveform for the same CAD patient depicted in FIG. 31 after PTCA, in accordance with various embodiments.

FIG. 32 is an exemplary time domain plot 3200 of an EPCG multi-domain ECG waveform for the same CAD patient depicted in FIG. 31 after PTCA, in accordance with various embodiments. A comparison of traditional ECG waveform 3120 of FIG. 31 and traditional ECG waveform 3220 of FIG. 32 shows that traditional or conventional ECG shows no specific change in ST-T before and after PTCA treatment.

However, a comparison of EPCG waveform 3110 of FIG. 31 and EPCG waveform 3210 of FIG. 32 shows that these EPCG provide a significant difference before and after treatment. More specifically, a comparison of the area near arrow 3130 in FIG. 31 with the area near arrow 3230 in FIG. 32 shows a major difference. Before treatment, it is not possible to discern subwaveforms near arrow 3130 of EPCG waveform 3110 in FIG. 31. However, after treatment, five subwaveforms are easily found near arrow 3230 of EPCG waveform 3210 in FIG. 32. FIGS. 31 and 32, therefore, show that EPCG can be used to diagnose diseases such as CAD, which cannot be easily diagnosed using traditional ECG.

Figure 33:
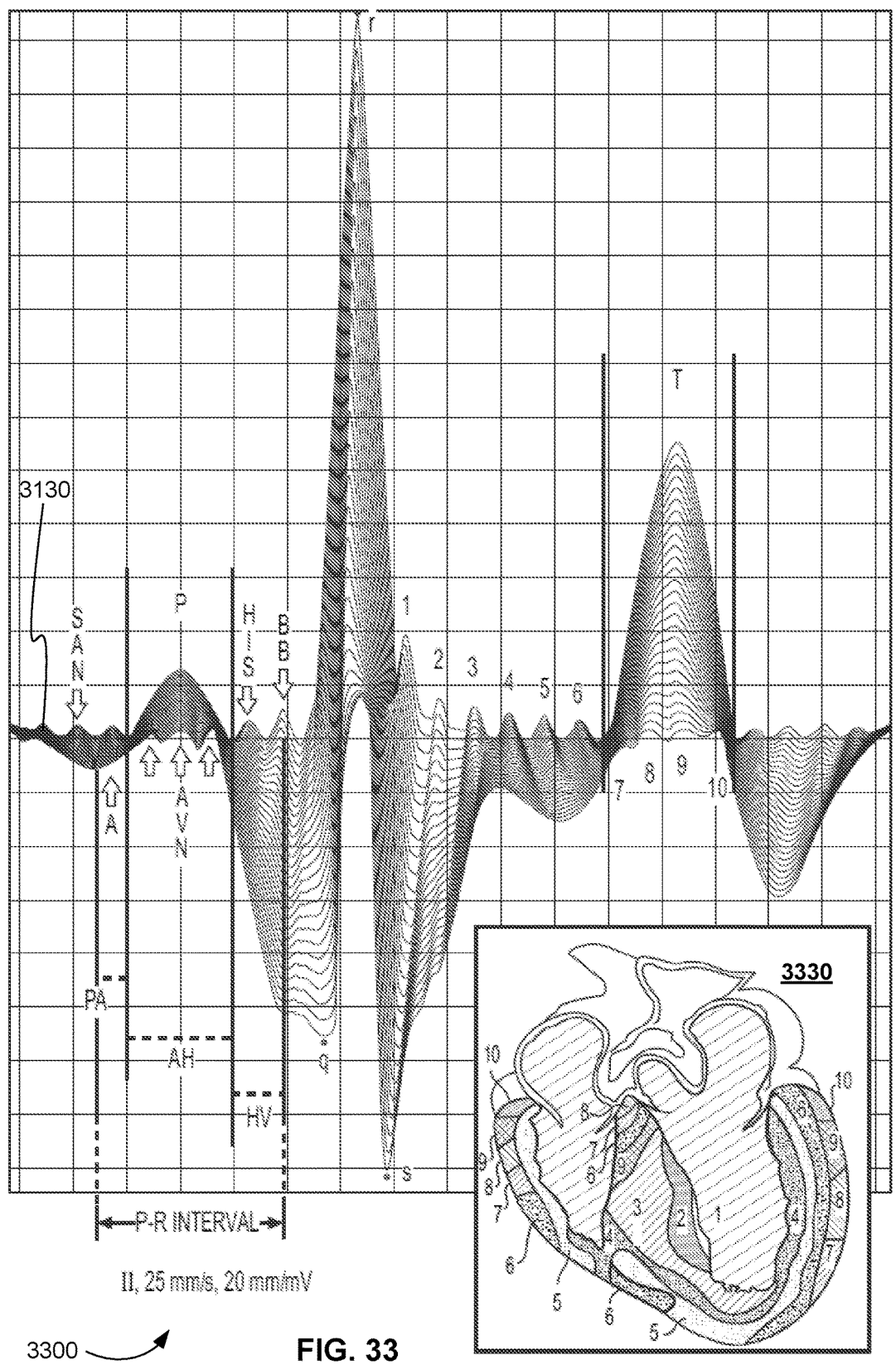
FIG. 33 is an exemplary time domain plot from an EPCG showing a multi-domain ECG waveform, showing cardiac electrophysiological markers for a single beat of a normal heart, and showing the locations of the myocardium markers on a heart diagram, in accordance with various embodiments.

FIG. 33 is an exemplary time domain plot 3300 from an EPCG showing a multi-domain ECG waveform, showing cardiac electrophysiological markers for a single beat of a normal heart, and showing the locations of the myocardium markers on a heart diagram, in accordance with various embodiments. Diagram 3330 shows the locations of heart cells represented by myocardium markers 1, 2, 3, 4, 5, 6, 7, 8, 9, and 10 of EPCG waveform 3310.

System for Displaying a Multi-Domain ECG Waveform with Markers

In various embodiments, an electrocardiography (ECG) system is provided for detecting a multi-domain ECG waveform and displaying the multi-domain ECG waveform with cardiac electrophysiological markers. Returning to FIG. 8, the ECG system includes two or more electrodes 810, a detector 820, a signal processor 830, and a display device 840.

Two or more electrodes 810 are adapted to be located near a beating heart of a patient to receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on the surface of the heart or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses. In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor 830 receives the ECG waveform from detector 820. Signal processor 830 converts the ECG waveform to a frequency domain waveform. Signal processor 830 separates the frequency domain waveform into two or more different frequency domain waveforms using two or more different bandpass filters. Finally, signal processor 830 converts the two or more different frequency domain waveforms into two or more different time domain waveforms.

Signal processor 830 separates the frequency domain waveform into two or more different frequency domain waveforms by dividing the frequency band of the ECG waveform into two or more different frequency bands and filtering the two or more different frequency bands using the two or more different bandpass filters, for example. In various embodiments, each of the two or more different frequency bands has the same bandwidth. In various alternative embodiments, each of the two or more different frequency bands can have different bandwidths. In various embodiments, the two or more different frequency bands are contiguous across the frequency band of the ECG waveform. In various alternative embodiments, the two or more different frequency bands are not contiguous across the frequency band of the ECG waveform.

Signal processor 830 can be a separate device, can be software running on device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general purpose processor. A general purpose processor can include, but is not limited to, a microprocessor, a micro controller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820.

Display device 840 displays the two or more different time domain waveforms in the same time domain plot as the ECG waveform for the at least one heartbeat of the beating heart. In addition, display device 840 displays one or more cardiac electrophysiological markers along the x-axis of the two or more different time domain waveforms. For example, a cardiac electrophysiological marker is placed along the x-axis of the two or more different time domain waveforms at a time location or within an interval of one or more subwaveforms. The one or more subwaveforms are subwaveforms representing the conduction through one or more groups of heart cells represented by the cardiac electrophysiological marker. The one or more cardiac electrophysiological markers can be placed at the time locations for a normal heart, or can be placed at locations inferred from the two or more different time domain waveforms.

In various embodiments, the one or more cardiac electrophysiological markers are heart cell markers. The heart cell markers can be cardiac self-conduction markers or myocardium markers.

In various embodiments, a cardiac self-conduction marker is shown along the x-axis of the two or more different time domain waveforms. It can further include an arrow pointing to the location or time location of a subwaveform representing conduction through a type of heart cells or fibers specified by the cardiac self-conduction marker.

A cardiac self-conduction marker can be a marker representing the time location of a subwaveform representing conduction through the sinoatrial node (S:SANODE) or through the atrium (A:ATRIAL). It can be a marker representing the time location of a subwaveform representing conduction through a first location in the atrioventricular node (N1:AV NODE (AN)), a second location in the atrioventricular node (N2:AV NODE (N)), or a third location in the atrioventricular node (N3:AV NODE (NH)). It can be a marker representing the time location of a subwaveform representing conduction through the His bundle (H: HIS BUNDLE), the bundle branches (B:BUNDLE BRANCHES), or the Purkinje fibers (P:PURKINJE'S).

In various embodiments, the one or more heart cell markers can be one or more myocardium markers. A myocardium marker is shown, for example, as delimiting a region along the x-axis of the two or more different time domain waveforms in which a subwaveform representing conduction through a particular location of the myocardium is specified by the myocardium marker. The one or more myocardium markers can be numbered, for example.

In various embodiments, the one or more cardiac electrophysiological markers can include one or more electrophysiological interval markers. The one or more electrophysiological interval markers are delimited regions along the x-axis of the two or more different time domain waveforms. These one or more electrophysiological interval markers can include a PA interval, an AH interval, and an HV interval.

The PA interval is the interval from the onset of the P wave to the onset of an atrial intracardiac signal. The AH interval is the conduction time through the AV node. The HV interval is the conduction time from the His bundle to the first ventricular activation.

As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record multi-domain ECG waveforms, saah multi-domain ECG data and conventional ECG waveforms and data. The memory device can be, but is not limited to, a volatile electronic memory, such as random access memory (RAM), a non-volatile electronic memory, such as electrically erasable programmable read-only memory (EEPROM or Flash memory), or a magnetic hard drive.

Method for Displaying a Multi-Domain ECG Waveform with Markers

Figure 34:
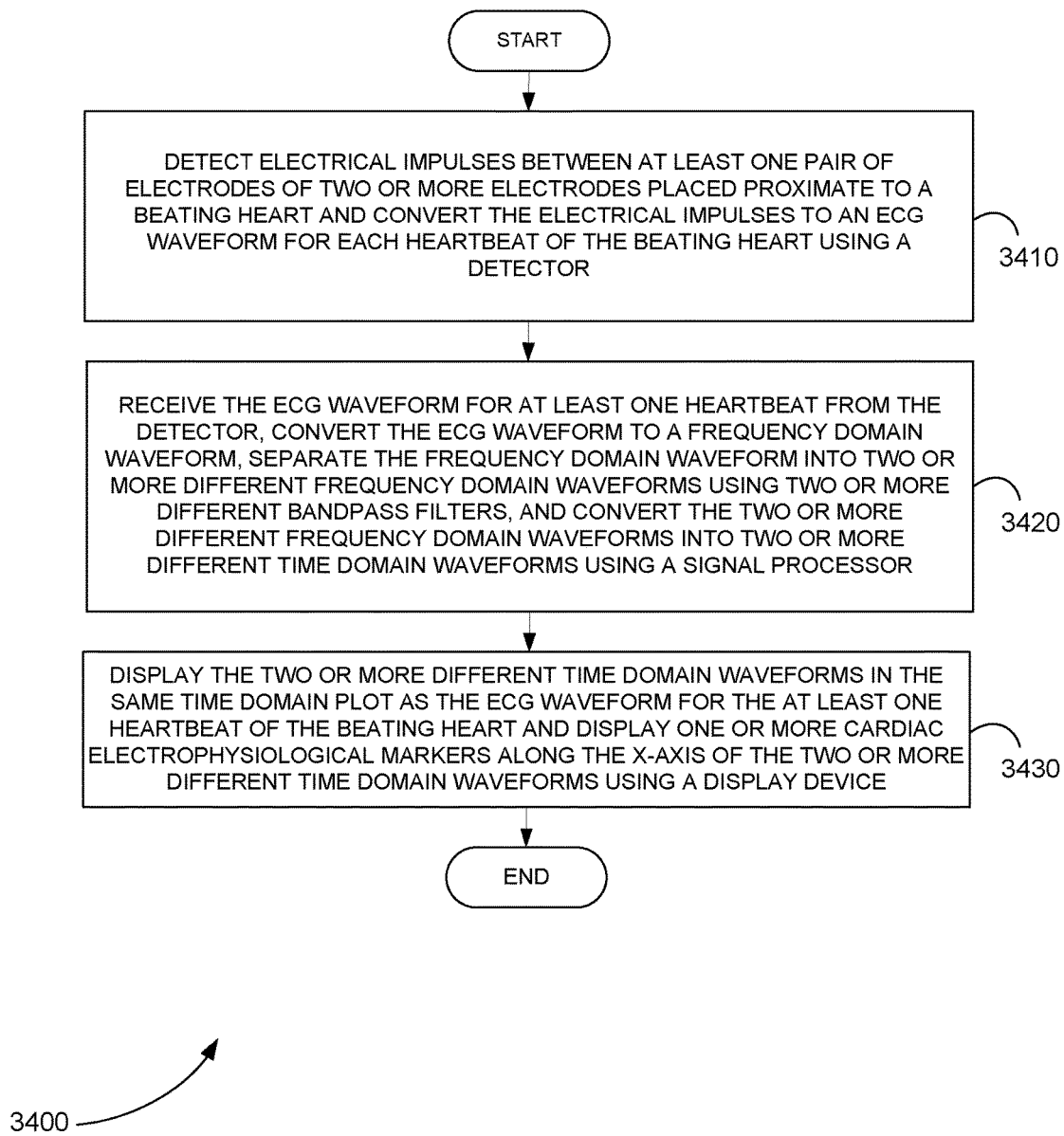
FIG. 34 is a flowchart showing a method for detecting a multi-domain ECG waveform and displaying the multi-domain ECG waveform with cardiac electrophysiological markers, in accordance with various embodiments.

FIG. 34 is a flowchart showing a method 3400 for detecting a multi-domain ECG waveform and displaying the multi-domain ECG waveform with cardiac electrophysiological markers, in accordance with various embodiments.

In step 3410 of method 3400, electrical impulses are detected between at least one pair of electrodes of two or more electrodes located near a beating heart of a patient and attached to the skin of the patient using a detector. The electrical impulses are converted to an ECG waveform for each heartbeat of the beating heart using the detector.

In step 3420, the ECG waveform for at least one heartbeat is received from the detector, the ECG waveform is converted to a frequency domain waveform, the frequency domain waveform is separated into two or more different frequency domain waveforms using two or more different bandpass filters, and the two or more different frequency domain waveforms are converted into two or more different time domain waveforms using a signal processor.

In step 3430, the two or more different time domain waveforms are displayed in the same time domain plot as the ECG waveform for the at least one heartbeat of the beating heart and one or more cardiac electrophysiological markers are displayed along the x-axis of the two or more different time domain waveforms using a display device. A cardiac electrophysiological marker is placed along the x-axis of the two or more different time domain waveforms at a time location or within an interval of one or more subwaveforms of one or more groups of heart cells represented by the cardiac electrophysiological marker.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A noninvasive electrocardiography (ECG) system for detecting a multi-domain ECG waveform and displaying cardiac electrophysiological markers with the multi-domain ECG waveform, comprising:

two or more electrodes adapted to be located near a beating heart of a patient and attached to the skin of the patient that receive electrical impulses from the beating heart;

a detector that detects the electrical impulses from at least one pair of electrodes of the two or more electrodes and converts the electrical impulses to an ECG waveform for each heartbeat of the beating heart;

a signal processor that receives the ECG waveform for at least one heartbeat from the detector, converts the ECG waveform to a frequency domain waveform, separates the frequency domain waveform into two or more different frequency domain waveforms using two or more different bandpass filters, and converts the two or more different frequency domain waveforms into two or more different time domain waveforms; and a display device that displays the two or more different time domain waveforms on the same time line in the same time domain plot as one multi-domain ECG waveform for the at least one heartbeat of the beating heart and displays one or more cardiac electrophysiological markers, wherein a cardiac electrophysiological marker is placed along the x-axis of the two or more different time domain waveforms at a time location or within an interval of one or more subwaveforms of one or more groups of heart cells represented by the cardiac electrophysiological marker.

2. The ECG system of claim 1, wherein the one or more cardiac electrophysiological markers comprise one or more heart cell markers.

3. The ECG system of claim 2, wherein the one or more heart cell markers comprise one or more cardiac self-conduction markers.

4. The ECG system of claim 3, wherein a cardiac self-conduction marker is shown along the x-axis of the two or more different time domain waveforms with an arrow pointing to the time location of a subwaveform representing conduction through a type of heart cells or fibers specified by the cardiac self-conduction marker.

5. The ECG system of claim 3, wherein the one or more cardiac self-conduction markers comprise a marker representing the time location of a subwaveform representing conduction through the sinoatrial node (S:SANODE).

6. The ECG system of claim 3, wherein the one or more cardiac self-conduction markers comprise a marker representing the time location of a subwaveform representing conduction through the atrium (A:ATRIAL).

7. The ECG system of claim 3, wherein the one or more cardiac self-conduction markers comprise a marker representing the time location of a subwaveform representing a first location in the atrioventricular node (N1:AV NODE (AN)).

8. The ECG system of claim 3, wherein the one or more cardiac self-conduction markers comprise a marker representing the time location of a subwaveform representing a second location in the atrioventricular node (N2:AV NODE (N)).

9. The ECG system of claim 3, wherein the one or more cardiac self-conduction markers comprise a marker representing the time location of a subwaveform representing a third location in the atrioventricular node (N3:AV NODE (NH)).

10. The ECG system of claim 3, wherein the one or more cardiac self-conduction markers comprise a marker representing the time location of a subwaveform representing conduction through the His bundle (H: HIS BUNDLE).

11. The ECG system of claim 3, wherein the one or more cardiac self-conduction markers comprise a marker representing the time location of a subwaveform representing conduction through the bundle branches (B:BUNDLE BRANCHES).

12. The ECG system of claim 3, wherein the one or more cardiac self-conduction markers comprise a marker representing the time location of a subwaveform representing conduction through the Purkinje fibers (P:PURKINJE'S).

13. The ECG system of claim 2, wherein the one or more heart cell markers comprise one or more myocardium markers.

14. The ECG system of claim 13, wherein a myocardium marker is shown as delimiting a region along the x-axis of the two or more different time domain waveforms in which a subwaveform representing conduction through a particular location of the myocardium is specified by the myocardium marker.

15. The ECG system of claim 13, wherein the one or more myocardium markers are numbered.

16. The ECG system of claim 1, wherein the one or more cardiac electrophysiological markers comprise one or more electrophysiological interval markers that are delimited regions along the x-axis of the two or more different time domain waveforms.

17. The ECG system of claim 16, wherein an electrophysiological interval marker comprises a PA interval, wherein the PA interval is the interval from the onset of the P wave to the onset of an atrial intracardiac signal.

18. The ECG system of claim 16, wherein an electrophysiological interval marker comprises an AH interval, wherein the AH interval is the conduction time through the AV node.

19. The ECG system of claim 16, wherein an electrophysiological interval marker comprises an HV interval, wherein the HV interval is the conduction time from the His bundle to the first ventricular activation.

20. An invasive electrocardiography (ECG) system for detecting a multi-domain ECG waveform and displaying cardiac electrophysiological markers with the multi-domain ECG waveform, comprising:

two or more electrodes placed directly on a surface of a beating heart of a patient that receive electrical impulses from the beating heart;

a detector that detects the electrical impulses from at least one pair of electrodes of the two or more electrodes and converts the electrical impulses to an ECG waveform for each heartbeat of the beating heart;

a signal processor that receives the ECG waveform for at least one heartbeat from the detector, converts the ECG waveform to a frequency domain waveform, separates the frequency domain waveform into two or more different frequency domain waveforms using two or more different bandpass filters, and converts the two or more different frequency domain waveforms into two or more different time domain waveforms; and a display device that displays the two or more different time domain waveforms on the same time line in the same time domain plot as one multi-domain ECG waveform for the at least one heartbeat of the beating heart and displays one or more cardiac electrophysiological markers, wherein a cardiac electrophysiological marker is placed along the x-axis of the two or more different time domain waveforms at a time location or within an interval of one or more subwaveforms of one or more groups of heart cells represented by the cardiac electrophysiological marker.

* * * * *